US007435804B2

(12) United States Patent
Kordyum et al.

(10) Patent No.: US 7,435,804 B2
(45) Date of Patent: Oct. 14, 2008

(54) METHOD FOR OBTAINING SINGLE CHAIN ANTIBODIES TO HUMAN INTERFERON α2B

(75) Inventors: Vitaliy A. Kordyum, Kyiv (UA); Oleg Okunev, Kyiv (UA); Pavlo Gilchuk, Kyiv (UA); Olena Deryabina, Kyiv (UA); Dmitro Irodov, Kyiv (UA)

(73) Assignee: Phage Biotechnology, Inc., Las Vegas, NV (US)

( * ) Notice: Subject to any disclaimer, the term of this patent is extended or adjusted under 35 U.S.C. 154(b) by 294 days.

(21) Appl. No.: 10/968,757

(22) Filed: Oct. 19, 2004

(65) Prior Publication Data

US 2006/0105389 A1 May 18, 2006

(51) Int. Cl.
| | |
|---|---|
| *C12P 21/08* | (2006.01) |
| *C12P 21/06* | (2006.01) |
| *C07K 16/00* | (2006.01) |
| *G01N 33/53* | (2006.01) |
| *C12N 1/20* | (2006.01) |
| *C12N 15/74* | (2006.01) |
| *C07H 21/04* | (2006.01) |
| *C40B 30/02* | (2006.01) |
| *C40B 40/02* | (2006.01) |

(52) U.S. Cl. .................. 530/388.8; 530/387.1; 435/7.1; 435/252.33; 435/488; 435/69.1; 536/23.53

(58) Field of Classification Search .............. 530/388.8, 530/387.1; 435/7.1, 252.33, 488, 69.1; 536/23.53
See application file for complete search history.

(56) References Cited

OTHER PUBLICATIONS

Casset et al. ((2003) BBRC 307, 198-205).*
Holm et al (Molec. Immunol. (2007) 44, 1075-1084).*
MacCallum et al. (J. Mol. Biol. (1996) 262, 732-745).*
Better, et al. "*Escherichia coli* Secretion of an Active Chimeric Antibody Fragment," *Science*, vol. 240, No. 4855, pp. 1041-1043, May 20, 1988.
Bird, et al. "Single-Chain Antigen-Binding Proteins," *Science*, vol. 242, No. 4877, pp. 423-426, Oct. 21, 1988.
Boss, et al. "Assembly of Functional Antibodies from Immunoglobulin Heavy and Light Chains Synthesised in *E. coli*," *Nucleic Acids Research*, vol. 12, No. 9, pp. 3791-3806, 1984.
Cabilly, "Generation of Antibody Activity from Immunoglobulin Polypeptide Chains Produced in *Escherichia coli*," *Proceedings of the National Academy of Sciences*, vol. 81, pp. 3273-3277, Jun. 1984.
Cheadle, et al. "Cloning and Expression of the Variable Regions of Mouse Myeloma Protein MOPC315 in *E. coli* Recovery of Active $F_v$ Fragments," *Molecular Immunology*, vol. 29, No. 1, pp. 21-30, 1992.
de Bernardez Clark, "Refolding of Recombinant Proteins," *Current Opinion in Biotechnology*, vol. 9, pp. 157-163, 1998.
Denèfle, et al. "Heterologous Protein in *Escherichia coli*: Influence of Bacterial Signal Peptides on the Export of Human Interleukin 1β," *Gene*, vol. 85, pp. 499-510, 1989.
Field, et al. "Expression of Mouse Immunoglobulin Light and Heavy Chain Variable Regions in *Escherichia coli* and Reconstruction of Antigen-Binding Activity" *Protein Engineering*, vol. 3, No. 7, pp. 641-647, 1989.
Ghrayeb, et al. "Secretion Cloning Vectors in *Escherichia coli*," *The EMBO Journal*, vol. 3, No. 10, pp. 2437-2442, 1984.
Glansbeek, et al. "Expression of recombinant Human Soluble Type II Transforming Growth Factor-β Receptor in *Pichia pastoris* and *Escherichia coli*: Two Powerful Systems to Express a Potent Inhibitor of Transforming Growth Factor-β," *Protein Expression and Purification*, vol. 12, pp. 201-207, 1998.
Goldstein, et al. "Enhancement of Protein Translocation Across the Membrane by Specific Mutations in the Hydrophobic Region of the Signal Peptide," *Journal of Bacteriology*, vol. 172, No. 3, pp. 1225-1231, 1990.
Hoffman, et al. "Fusions of Secreted Proteins to Alkaline Phosphatase: An Approach for Studying Protein Secretion," *Proceedings of the National Academy of Sciences*, vol. 82, pp. 5107-5111, Aug. 1985.
Huse, et al. "Generation of a Large Combinatorial Library of the Immunoglobulin Repertoire in Phage Lambda," *Science*, vol. 246, pp. 1275-1281, Dec. 1989.
Huston, et al. "Protein Engineering of Antibody Binding Sites: Recovery of Specific Activity in an Anti-Digoxin Singe-Chain Fv Analogue Produced in *Escherichia coli*," *Proceedings of the National Academy of Sciences*, vol. 85, pp. 5879-5883, Aug. 1988.
Johnson, et al. "Refolding, Purification, and Characterization of Human Erythropoietin Binding Protein Produced in *Escherichia coli*," *Protein Expression and Purification*, vol. 7, pp. 104-113, 1996.
Kadonaga, et al. "The Role of the β-Lactamase Signal Sequence in the Secretion of Proteins by *Escherichia coli*," *The Journal of Biological Chemistry*, vol. 259, No. 4, pp. 2149-2154, Feb. 25, 1984.
Kurucz, et al. "Correct Disulfide Pairing and Efficient Refolding of Detergent-Solubilized Single-Chain Fv Proteins from Bacterial Inclusion Bodies," *Molecular Immunology*, vol. 32, pp. 1443-1452, 1995.
Lei, et al. "Characterization of the *Erwinia carotovora peIB* Gene and its Product Pectate Lyase," *Journal of Bacteriology*, vol. 169, No. 9, pp. 4379-4383, Sep. 1987.

(Continued)

*Primary Examiner*—David J. Blanchard
*Assistant Examiner*—Lynn Bristol
(74) *Attorney, Agent, or Firm*—Knobbe, Martens, Olson & Bear, LLP

(57) ABSTRACT

A bacterial high-expression system which is applicable for simultaneous screening of large numbers of recombinant clones from combinatorial antibody libraries is disclosed. The method pertains to screening of single chain antibodies from libraries expressed in the periplasm of *E. coli* by secretion. By this approach, approximately $10^4$ clones can be screened in a single round. After screening, the clones, which express the recombinant antibodies to the desired antigen, can be directly used for production of large quantities of antibodies from microorganism culture. The system is especially attractive for fast screening of antibody libraries from a hybridoma source. A refolding method for the large-scale production of biologically active scFv-6 his proteins from bacterial inclusion bodies is also disclosed.

10 Claims, 14 Drawing Sheets

OTHER PUBLICATIONS

Lindner, et al. "Purification of Native Proteins from the Cytoplasm and Periplasm of *Escherichia coli* Using IMAC and Histidine Tails: A Comparison of Proteins and Protocols," *A Companion to Methods in Enzymology*, vol. 4, pp. 41-56, 1992.

Marston, et al. "Solubilization of Protein Aggregates," *Methods in Enzymology*, vol. 182, pp. 264-276, 1990.

Holzinger, et al. "Single-Step Purification/Solubilization of Recombinant Proteins: Application to Surfactant Protein B," *BioTechniques*, vol. 20, No. 5, pp. 804-808, 1996.

Pantoliano, et al. "Conformational Stability, Folding, and Ligand-Binding Affinity of Single-Chain Fv Immunoglobulin Fragments Expressed in *Escherichia coli*," *Biochemistry*, vol. 30, pp. 10117-10125, 1991.

Raag, et al. "Single-Chain Fvs," *The FASEB Journal*, vol. 9, pp. 73-79, Jan. 1995.

Rudolph, et al. "In Vitro Folding of Inclusion Body Proteins," *The FASEB Journal*, vol. 10, pp. 49-56, Jan. 1996.

Skerra, Bacterial Expression of Immunoglobulin Fragments, *Current Opinion in Immunology*, vol. 5, pp. 256-262, 1993.

Smith, et al. "Phage Display," *Chemical Review*, vol. 97, pp. 391-410, 1997.

* cited by examiner

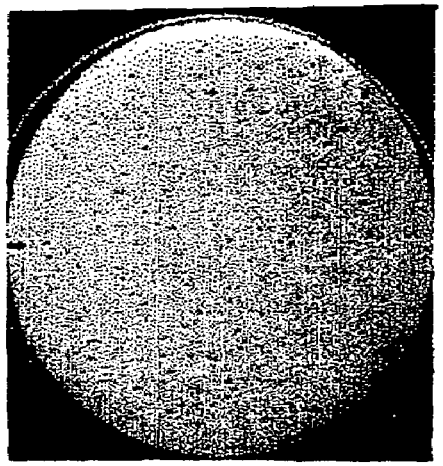
FIG. 1A
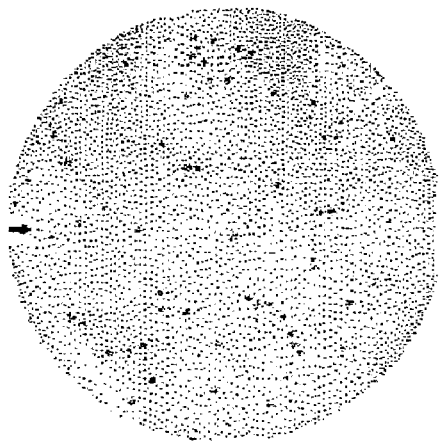
FIG. 1B
FIG. 2A
FIG. 2B
FIG. 2C
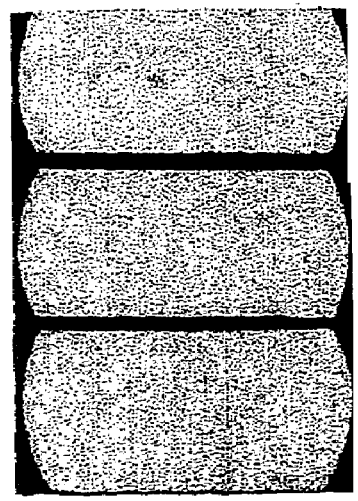

```
  1  ATGAAAAAATTATTATTCGCAATTCCTTTAGTTGTTCCTTTCTATGCGGC
 51  CCAGCCGGCCATGGCCCACGTGAAGCTGCAGCAGTCTGGGGCAGAGCTTG
101  TGAAGCCAGGGGCCTCAGTCAAGTTGTCCTGCACAGCTTCTGGCTTCAAC
151  ATTAAAGACACCTTTATTCACTGGGTGAAGCAGAGGCCTGAACAGGGCCT
201  GGAGTGGATTGGAAGGATTGATCCTGCGAATGGTTATACTAAATATGACC
251  CGAACTTCCAGGGCAAGGCCACTATAACAGCAGACACATCCTCCAACACA
301  GCCTACCTGCAGCTCAGCAGCCCGACATCTGAGGGCACTGCCGTCTATTA
351  CTGTGCTAGCAGAGTAGACTATGCTATGGACTACTGGGGCCAAGGCACCA
401  CGGTCACCGTCTCCTCAGGTGGAGGCGGTTCAGGCGGAGGTGGCTCTGGC
451  GGTGGCGGATCGGACATCGAGCTCACTCAGTCTCCAGCCACCCTGTCTGT
501  GACAGCAGGAGAGAAGGTCACTATGAGTTGCAAGTCCAGTCAGAGTCTGT
551  TAAACAGTGGAAATCAAAAGAACTACTTGACCTGGTACCAGCAGAAACCA
601  GGGCAGCCTCCTAAACTGTTGATCTACTGGGCATCCACCAGGGAATCTGG
651  GGTCCCTGATCGCTTCACAGGCAGTGGATATGGAACAGATTTCACTCTCA
701  CCATCAGCAGTGTGCAGGCTGAAGACCTGGCAGTTTATTACTGTCAGAAT
751  GATTATAGTTATCCGCTCACGTTCGGTGCTGGCACCAAGCTGGAAATCAA
801  ACGGGCGGCCGCACTCGAGCACCACCACCACCACAAGTGA
```

FIG. 6

```
  1  MKKLLFAIPLVVPFYAAQPAMAHVKLQQSGAELVKPGASVKLSCTASGFN
 51  IKDT FIH W V KQRPEQGLE WIGRIDPANG YTKYDPNFQ GKAT IT  AD  T    SNT
                                                             S
101  AYLQLSSPTSEGTAVYYCASRVDYAMDYWGQGTTVTVSSGGGGSGGGGSG
151  GGGSDIELTQSPATLSVTAGEKVTMSCKSSQSLLNSGNQKNYLTWYQQKP
201  GQPPKLLIYWASTRESGVPDRFTGSGYGTDFTLTISSVQAEDLAVYYCQN
251  DY SYPLTFGAGTKLEIKRAAALEHHHHHH
```

FIG. 7 bp   1- 60: synthetic signal sequence  
bp  61-411: heavy chain variable domain  
bp 412- 462: 2Ser (Gly$_4$ Ser)$_3$ linker  
bp 463- 807: light chain variable domain  
bp 808-819: site for XhoI  
bp 820-837: His 6 tag  
bp 838-840: stop codon

FIG. 8

*VH amino acid sequence*

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|
| M | A | H | V | K | L | Q | Q | S | G | A | E | L | V | K | P | G | A | S | V | K | L | S | C | T | A |

| 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|
| S | G | H | N | I | K | D | T | F | I | H | W | V | K | Q | R | P | E | Q | G | L | E | W | I | G | R |

| 52A | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 |
|---|---|---|---|---|---|---|---|---|---|---|---|---|---|---|---|---|---|---|---|---|---|---|---|---|---|
| I | D | P | A | N | G | Y | T | K | Y | D | P | N | F | Q | G | K | A | T | I | T | A | D | T | S | S |

| 78 | 79 | 80 | 81 | 82 | 82A | 82B | 82C | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|---|---|---|---|---|---|
| N | T | A | Y | L | Q | L | S | S | P | T | S | E | G | T | A | V | Y | Y | C | A | S | R | V | D | Y |

| 100A | 100B | 101 | 102 | 103 | 104 | 105 | 106 | 107 | 108 | 109 | 110 | 111 | 112 | 113 |
|---|---|---|---|---|---|---|---|---|---|---|---|---|---|---|
| A | M | D | Y | - | - | W | G | Q | G | T | T | V | T | V |

*VL amino acid sequence*

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|
| D | I | E | L | T | Q | S | P | A | T | L | S | V | T | A | G | E | K | V | T | M | S | C | K | S | S |

| 27 | 27A | 27B | 27C | 27D | 27E | 27F | 28 | 29 | 30 | 31 | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|---|---|---|---|---|---|---|---|---|---|
| Q | S | L | L | N | S | G | N | Q | K | N | Y | L | T | W | Y | Q | Q | K | P | G | Q | P | P | K | L |

| 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|---|---|---|---|---|---|---|---|---|
| L | I | Y | W | A | S | T | R | E | S | G | V | P | D | R | F | T | G | S | G | Y | G | T | D | F | T |

| 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 |
|---|---|---|---|---|---|---|---|---|---|---|---|---|---|---|---|---|---|---|---|---|---|---|---|---|---|
| L | T | I | S | S | V | Q | A | E | D | L | A | V | Y | Y | C | Q | N | D | Y | S | Y | P | L | T | F |

| 99 | 100 | 101 | 102 | 103 | 104 | 105 | 106 | 106A | 107 | 108 | 109 |
|---|---|---|---|---|---|---|---|---|---|---|---|
| G | A | G | T | K | L | E | I | - | K | R | A |

FIG. 9

```
     Rank GenPept code                                                                SEQ ID
                                                                                      NO:

1_17662    1   MAHVKLQQSGAELVKPGASVKLSCTASGFNIKDTFIHWVKQRPEQGLEWIGRIDPANG 58    11
     1.   347913     2    .Q............................YM........................ 56    13
     2.   4138227    1   ..Q.........R.................Y.....................N.... 58    14
     3.   195064    10   SE.Q...........................YM........................ 66    15
     4.   1518301    3    .Q............................YM........................ 57    16
     5.   195748    19   SE.Q........R..................YM........................ 75    17
     6.   11514087   2   ...............................YM........................ 56    18
     7.   2209229   19   SE.Q..........................Y.....................I. 75    19
     8.   347917     2    .Q............................YM........................ 56    20
     9.   5690295    2    .Q.................S..........YM........................ 56    21
     10.  346840    13   SE.Q...........................YM.......K................ 69    22

1_17662   59   YTKYDPNFQGKATITADTSSNTAYLQLSSPTSEGTAVYYC-A-------S----R-V--D 103
     1.   347913    57   N.....K.....................L...D......-.-------R-----A--S 101
     2.   4138227   59   I.T...K.....................L...D....F.---------T----.-.--P 102
     3.   195064    67   N.....K.....................L...D......-.-------RGGL-.-R--G 114
     4.   1518301   58   N.....K.....................L...D......-.-------R-----.-E--L 102
     5.   195748    76   N.....K...........T.........L...D......-.-------.----Y-Y--R 120
     6.   11514087  57   N.....K.....................L...D......-.--------------.-W--. 100
     7.   2209229   76   N.....K.....................L...D......-S-------R----G-I--T 120
     8.   347917    57   N.....K.....................L...D......-V--------.--------S  99
     9.   5690295   57   N.....K.....................L...D......-.-------R----W-LLRY 103
     10.  346840    70   ..E...K...........T.........L...D......TG-------G----N-Y--A 115

1_17662  140   ---Y--A--MDYWGQGTTVTV 117
     1.   347913   102   ---.---.--........S... 115
     2.   4138227  103   ---.------F........... 115
     3.   195064   115   ---.---.--........S... 128
     4.   1518301  103   ---.--Y--F........P... 116
     5.   195748   121   YPY.---.--........S... 137
     6.   11514087 101   ---W--Y--F.V.......... 114
     7.   2209229  121   PY-.---.--I.......S... 136
     8.   347917   100   ---.---.--........S... 113
     9.   5690295  104   ---.---.--........S... 117
     10.  346840   116   ---.--G--.........S... 129
```

Fig. 10 Sequence alignment VH ScFv 17(IFN) with GentPept protein database

```
        Rank GenPept code                                                                        SEQ ID
                                                                                                 NO:

1_24712    1   DIELTQSPATLSVTAGEKVTMSCK-SSQSLLNSGNQKNYLTWYQQKPGQPPKLL------  53          12
1.       6272271  135   ..V.....SS.T...........-..............................------ 187          23
2.       1360012  130   .......SS.T.....R......-............H.................------ 182          24
3.      31088009  423   .......SS.T.........N..-........R......................------ 475         25
4.      20797200    1   .......SS.T.........N..-........R......................------  53          26
5.        196563    1   ..VM....SS.T...........-...............................------  53          27
6.      28316378    1   ..QM...TSS.T...........-...............................------  53          28
7.        196571    1   ..VM....SS.T...........-...............................------  53          29
8.        230159    1   ..VM....SS...S...R.....-.................F.A..........------  53          30
9.        208622    2   ..VM....SS...S...R.....-.................F.A..........------  54          31
10.       196565    1   ..VM....SS.T...........-...............................------  53          32

1_24712   54   -IYWA---STRESGVPDR--FTGSGYGTDFTLTISSVQAEDLAVYYC-QND--YSYPLT- 103
1.       6272271  188   -....---..........--.....S....................-....F.- 237
2.       1360012  183   -....---..........--.....S....................-....F.YP- 232
3.      31088009  476   -....---..........--.....S....................-....V....- 525
4.      20797200   54   -....---..........--.....S....................-....V....- 103
5.        196563   54   -....---..........--.....S....................-.........- 103
6.      28316378   54   -....---..........--.....S....................-.........- 103
7.        196571   54   -....---..........--.....S....................-.........- 103
8.        230159   54   -...G.---..........--.....S....................-...-H.....- 103
9.        208622   55   -...G.---..........--.....S....................-...-H.....- 104
10.       196565   55   -....---..........--.....S.......X............-.........- 103

1_24712  104   --FGAGTKLEIKRA 115
1.       6272271  238   --..S........ 248
2.       1360012  233   --..G........ 244
3.      31088009  526   --........... 536
4.      20797200  104   --........... 114
5.        196563  104   --........L.. 114
6.      28316378  104   --........L.. 115
7.        196571  104   --..S........ 114
8.        230159  104   --........... 115
9.        208622  105   --........L.. 116
10.       196565  104   --........L.. 114
```

Fig. 11 Sequence alignment VL ScFv 17(IFN) with GentPept protein database

SEQUENCE LISTING

<160> NUMBER OF SEQ ID NOS: 33

<210> SEQ ID NO 1
<211> LENGTH: 843
<212> TYPE: DNA
<213> ORGANISM: Mus musculus
<220> FEATURE:
<221> NAME/KEY: sig_peptide
<222> LOCATION: (1)...(60)
<220> FEATURE:
<221> NAME/KEY: misc_feature
<222> LOCATION: (61)...(411)
<223> OTHER INFORMATION: heavy chain variable domain
<220> FEATURE:
<221> NAME/KEY: misc_feature
<222> LOCATION: (412)...(462)
<223> OTHER INFORMATION: linker
<220> FEATURE:
<221> NAME/KEY: misc_feature
<222> LOCATION: (463)...(807)
<223> OTHER INFORMATION: light chain variable domain
<220> FEATURE:
<221> NAME/KEY: misc_feature
<222> LOCATION: (808)...(819)
<223> OTHER INFORMATION: Xho1 site
<220> FEATURE:
<221> NAME/KEY: misc_feature
<222> LOCATION: (820)...(837)
<223> OTHER INFORMATION: His 6 tag
<220> FEATURE:
<221> NAME/KEY: terminator
<222> LOCATION: (838)...(840)
<223> OTHER INFORMATION: Stop codon

<400> SEQUENCE: 1

```
atgaaaaaat tattattcgc aattcctta gttgttcctt tctatgcggc ccagccggcc      60
atggcccacg tgaagctgca gcagtctggg gcagagcttg tgaagccagg ggcctcagtc     120
aagttgtcct gcacagcttc tggcttcaac attaaagaca cctttattca ctgggtgaag     180
cagaggcctg aacagggcct ggagtggatt ggaaggattg atcctgcgaa tggttatact     240
aaatatgacc cgaacttcca gggcaaggcc actataacag cagacacatc ctccaacaca     300
gcctacctgc agctcagcag cccgacatct gagggcactg ccgtctatta ctgtgctagc     360
agagtagact atgctatgga ctactgggc caaggcacca cggtcaccgt ctcctcaggt     420
ggaggcggtt caggcggagg tggctctggc ggtggcggat cggacatcga gctcactcag     480
tctccagcca ccctgtctgt gacagcagga gagaaggtca ctatgagttg caagtccagt     540
cagagtctgt taacagtgg aaatcaaaag aactacttga cctggtacca gcagaaacca     600
gggcagcctc ctaaactgtt gatctactgg gcatccacca gggaatctgg ggtccctgat     660
cgcttcacag gcagtggata tggaacagat ttcactctca ccatcagcag tgtgcaggct     720
gaagacctgg cagtttatta ctgtcagaat gattatagtt atccgctcac gttcggtgct     780
ggcaccaagc tggaaatcaa acgggcggcc gcactcgagc accaccacca ccaccacaag     840
tga                                                                  843
```

<210> SEQ ID NO 2
<211> LENGTH: 279
<212> TYPE: PRT
<213> ORGANISM: Mus musculus

<400> SEQUENCE: 2

```
Met Lys Lys Leu Leu Phe Ala Ile Pro Leu Val Val Pro Phe Tyr Ala
 1               5                  10                  15
```

```
Ala Gln Pro Ala Met Ala His Val Lys Leu Gln Gln Ser Gly Ala Glu
            20                  25                  30

Leu Val Lys Pro Gly Ala Ser Val Lys Leu Ser Cys Thr Ala Ser Gly
        35                   40                  45

Phe Asn Ile Lys Asp Thr Phe Ile His Trp Val Lys Gln Arg Pro Glu
    50                  55                  60

Gln Gly Leu Glu Trp Ile Gly Arg Ile Asp Pro Ala Asn Gly Tyr Thr
65                  70                  75                  80

Lys Tyr Asp Pro Asn Phe Gln Gly Lys Ala Thr Ile Thr Ala Asp Thr
                85                  90                  95

Ser Ser Asn Thr Ala Tyr Leu Gln Leu Ser Ser Pro Thr Ser Glu Gly
            100                 105                 110

Thr Ala Val Tyr Tyr Cys Ala Ser Arg Val Asp Tyr Ala Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Asp Ile Glu Leu Thr Gln
145                 150                 155                 160

Ser Pro Ala Thr Leu Ser Val Thr Ala Gly Glu Lys Val Thr Met Ser
                165                 170                 175

Cys Lys Ser Ser Gln Ser Leu Leu Asn Ser Gly Asn Gln Lys Asn Tyr
            180                 185                 190

Leu Thr Trp Tyr Gln Gln Lys Pro Gly Gln Pro Lys Leu Leu Ile
        195                 200                 205

Tyr Trp Ala Ser Thr Arg Glu Ser Gly Val Pro Asp Arg Phe Thr Gly
    210                 215                 220

Ser Gly Tyr Gly Thr Asp Phe Thr Leu Thr Ile Ser Ser Val Gln Ala
225                 230                 235                 240

Glu Asp Leu Ala Val Tyr Tyr Cys Gln Asn Asp Tyr Ser Tyr Pro Leu
                245                 250                 255

Thr Phe Gly Ala Gly Thr Lys Leu Glu Ile Lys Arg Ala Ala Ala Leu
            260                 265                 270

Glu His His His His His His
        275

<210> SEQ ID NO 3
<211> LENGTH: 117
<212> TYPE: PRT
<213> ORGANISM: Mus musculus

<400> SEQUENCE: 3

Met Ala His Val Lys Leu Gln Gln Ser Gly Ala Glu Leu Val Lys Pro
1               5                   10                  15

Gly Ala Ser Val Lys Leu Ser Cys Thr Ala Ser Gly Phe Asn Ile Lys
            20                  25                  30

Asp Thr Phe Ile His Trp Val Lys Gln Arg Pro Glu Gln Gly Leu Glu
        35                  40                  45

Trp Ile Gly Arg Ile Asp Pro Ala Asn Gly Tyr Thr Lys Tyr Asp Pro
    50                  55                  60

Asn Phe Gln Gly Lys Ala Thr Ile Thr Ala Asp Thr Ser Ser Asn Thr
65                  70                  75                  80

Ala Tyr Leu Gln Leu Ser Ser Pro Thr Ser Glu Gly Thr Ala Val Tyr
                85                  90                  95
```

```
Tyr Cys Ala Ser Arg Val Asp Tyr Ala Met Asp Tyr Trp Gly Gln Gly
            100                 105                 110

Thr Thr Val Thr Val
        115

<210> SEQ ID NO 4
<211> LENGTH: 115
<212> TYPE: PRT
<213> ORGANISM: Mus musculus

<400> SEQUENCE: 4

Asp Ile Glu Leu Thr Gln Ser Pro Ala Thr Leu Ser Val Thr Ala Gly
  1               5                  10                  15

Glu Lys Val Thr Met Ser Cys Lys Ser Gln Ser Leu Leu Asn Ser
             20                  25                  30

Gly Asn Gln Lys Asn Tyr Leu Thr Trp Tyr Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Thr Gly Ser Gly Tyr Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Ile
            100                 105                 110

Lys Arg Ala
        115

<210> SEQ ID NO 5
<211> LENGTH: 62
<212> TYPE: DNA
<213> ORGANISM: Artificial Sequence
<220> FEATURE:
<223> OTHER INFORMATION: chemically synthesized annealing
      oligonucleotide

<400> SEQUENCE: 5
tatgaaaaaa ttattattcg caattccttt agttgttcct ttctatgcgg cccagccggc    60
ca                                                                   62

<210> SEQ ID NO 6
<211> LENGTH: 64
<212> TYPE: DNA
<213> ORGANISM: Artificial Sequence
<220> FEATURE:
<223> OTHER INFORMATION: chemically synthesized annealing
      oligonucleotide

<400> SEQUENCE: 6
agcttggccg gctgggccgc atagaaagga caactaaag gaattgcgaa taataatttt    60
ttca                                                                 64

<210> SEQ ID NO 7
<211> LENGTH: 26
<212> TYPE: DNA
<213> ORGANISM: Artificial Sequence
<220> FEATURE:
<223> OTHER INFORMATION: chemically synthesized primer
```

<400> SEQUENCE: 7
ccatgattac gccaagcttt ggagcc                                26

<210> SEQ ID NO 8
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 8
cgatctaaag ttttgtcgtc tttcc                                 25

<210> SEQ ID NO 9
<211> LENGTH: 23
<212> TYPE: DNA
<213> ORGANISM: Artificial Sequence
<220> FEATURE:
<223> OTHER INFORMATION: chemically synthesized sequencing primer

<400> SEQUENCE: 9
ggttcaggcg gaggtggctc tgg                                   23

<210> SEQ ID NO 10
<211> LENGTH: 23
<212> TYPE: DNA
<213> ORGANISM: Artificial Sequence
<220> FEATURE:
<223> OTHER INFORMATION: chemically synthesized sequencing primer

<400> SEQUENCE: 10
ccagagccac ctccgcctga acc                                   23

<210> SEQ ID NO 11
<211> LENGTH: 117
<212> TYPE: PRT
<213> ORGANISM: Mus musculus

<400> SEQUENCE: 11

Met Ala His Val Lys Leu Gln Gln Ser Gly Ala Glu Leu Val Lys Pro
 1               5                  10                  15

Gly Ala Ser Val Lys Leu Ser Cys Thr Ala Ser Gly Phe Asn Ile Lys
             20                  25                  30

Asp Thr Phe Ile His Trp Val Lys Gln Arg Pro Glu Gln Gly Leu Glu
         35                  40                  45

Trp Ile Gly Arg Ile Asp Pro Ala Asn Gly Tyr Thr Lys Tyr Asp Pro
     50                  55                  60

Asn Phe Gln Gly Lys Ala Thr Ile Thr Ala Asp Thr Ser Ser Asn Thr
 65                  70                  75                  80

Ala Tyr Leu Gln Leu Ser Ser Pro Thr Ser Glu Gly Thr Ala Val Tyr
                 85                  90                  95

Tyr Cys Ala Ser Arg Val Asp Tyr Ala Met Asp Tyr Trp Gly Gln Gly
            100                 105                 110

Thr Thr Val Thr Val
        115

<210> SEQ ID NO 12
<211> LENGTH: 115
<212> TYPE: PRT
<213> ORGANISM: Mus musculus

<400> SEQUENCE: 12

Asp Ile Glu Leu Thr Gln Ser Pro Ala Thr Leu Ser Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Tyr Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Arg Ala
        115

<210> SEQ ID NO 13
<211> LENGTH: 114
<212> TYPE: PRT
<213> ORGANISM: Mus musculus

<400> SEQUENCE: 13

Val Gln Leu Gln Gln Ser Gly Ala Glu Leu Val Lys Pro Gly Ala Ser
1               5                   10                  15

Val Lys Leu Ser Cys Thr Ala Ser Gly Phe Asn Ile Lys Asp Thr Tyr
            20                  25                  30

Met His Trp Val Lys Gln Arg Pro Glu Gln Gly Leu Glu Trp Ile Gly
        35                  40                  45

Arg Ile Asp Pro Ala Asn Gly Asn Thr Lys Tyr Asp Pro Lys Phe Gln
    50                  55                  60

Gly Lys Ala Thr Ile Thr Ala Asp Thr Ser Ser Asn Thr Ala Tyr Leu
65                  70                  75                  80

Gln Leu Ser Ser Leu Thr Ser Glu Asp Thr Ala Val Tyr Tyr Cys Ala
                85                  90                  95

Arg Arg Ala Ser Tyr Ala Met Asp Tyr Trp Gly Gln Gly Thr Ser Val
            100                 105                 110

Thr Val

<210> SEQ ID NO 14
<211> LENGTH: 115
<212> TYPE: PRT
<213> ORGANISM: Mus musculus

<400> SEQUENCE: 14

Met Ala Gln Val Lys Leu Gln Gln Ser Gly Ala Glu Leu Val Lys Pro
1               5                   10                  15

Gly Ala Ser Val Arg Leu Ser Cys Thr Ala Ser Gly Phe Asn Ile Lys
            20                  25                  30

Asp Thr Tyr Ile His Trp Val Lys Gln Arg Pro Glu Gln Gly Leu Glu
        35                  40                  45

Trp Ile Gly Arg Ile Asn Pro Ala Asn Gly Ile Thr Thr Tyr Asp Pro
    50                  55                  60

Lys Phe Gln Gly Lys Ala Thr Ile Thr Ala Asp Thr Ser Ser Asn Thr
65                  70                  75                  80

```
Ala Tyr Leu Gln Leu Ser Ser Leu Thr Ser Glu Asp Thr Ala Val Tyr
                85                  90                  95

Phe Cys Thr Arg Val Pro Tyr Phe Asp Tyr Trp Gly Gln Gly Thr Thr
            100                 105                 110

Val Thr Val
        115

<210> SEQ ID NO 15
<211> LENGTH: 119
<212> TYPE: PRT
<213> ORGANISM: Mus musculus

<400> SEQUENCE: 15

Ser Glu Val Gln Leu Gln Gln Ser Gly Ala Glu Leu Val Lys Pro Gly
1               5                   10                  15

Ala Ser Val Lys Leu Ser Cys Thr Ala Ser Gly Phe Asn Ile Lys Asp
            20                  25                  30

Thr Tyr Met His Trp Val Lys Gln Arg Pro Glu Gln Gly Leu Glu Trp
        35                  40                  45

Ile Gly Arg Ile Asp Pro Ala Asn Gly Asn Thr Lys Tyr Asp Pro Lys
    50                  55                  60

Phe Gln Gly Lys Ala Thr Ile Thr Ala Asp Thr Ser Ser Asn Thr Ala
65                  70                  75                  80

Tyr Leu Gln Leu Ser Ser Leu Thr Ser Glu Asp Thr Ala Val Tyr Tyr
                85                  90                  95

Cys Ala Arg Gly Gly Leu Arg Arg Gly Tyr Ala Met Asp Tyr Trp Gly
            100                 105                 110

Gln Gly Thr Ser Val Thr Val
        115

<210> SEQ ID NO 16
<211> LENGTH: 114
<212> TYPE: PRT
<213> ORGANISM: Mus musculus

<400> SEQUENCE: 16

Val Gln Leu Gln Gln Ser Gly Ala Glu Leu Val Lys Pro Gly Ala Ser
1               5                   10                  15

Val Lys Leu Ser Cys Thr Ala Ser Gly Phe Asn Ile Lys Asp Thr Tyr
            20                  25                  30

Met His Trp Val Lys Gln Arg Pro Glu Gln Gly Leu Glu Trp Ile Gly
        35                  40                  45

Arg Ile Asp Pro Ala Asn Gly Asn Thr Lys Tyr Asp Pro Lys Phe Gln
    50                  55                  60

Gly Lys Ala Thr Ile Thr Ala Asp Thr Ser Ser Asn Thr Ala Tyr Leu
65                  70                  75                  80

Gln Leu Ser Ser Leu Thr Ser Glu Asp Thr Ala Val Tyr Tyr Cys Ala
                85                  90                  95

Arg Arg Glu Leu Tyr Tyr Phe Asp Tyr Trp Gly Gln Gly Thr Pro Val
            100                 105                 110

Thr Val

<210> SEQ ID NO 17
<211> LENGTH: 119
<212> TYPE: PRT
<213> ORGANISM: Mus musculus
```

<400> SEQUENCE: 17

Ser Glu Val Gln Leu Gln Gln Ser Gly Ala Glu Leu Val Arg Pro Gly
1               5                   10                  15

Ala Ser Val Lys Leu Ser Cys Thr Ala Ser Gly Phe Asn Ile Lys Asp
            20                  25                  30

Thr Tyr Met His Trp Val Lys Gln Arg Pro Glu Gln Gly Leu Glu Trp
        35                  40                  45

Ile Gly Arg Ile Asp Pro Ala Asn Gly Asn Thr Lys Tyr Asp Pro Lys
    50                  55                  60

Phe Gln Gly Lys Ala Thr Ile Thr Ala Asp Thr Ser Ser Asn Thr Ala
65                  70                  75                  80

Tyr Leu Gln Leu Ser Ser Leu Thr Ser Glu Asp Thr Ala Val Tyr Tyr
                85                  90                  95

Cys Ala Ser Tyr Tyr Arg Tyr Pro Tyr Tyr Ala Met Asp Tyr Trp Gly
            100                 105                 110

Gln Gly Thr Ser Val Thr Val
                115

<210> SEQ ID NO 18
<211> LENGTH: 113
<212> TYPE: PRT
<213> ORGANISM: Mus musculus

<400> SEQUENCE: 18

Val Lys Leu Gln Gln Ser Gly Ala Glu Leu Val Lys Pro Gly Ala Ser
1               5                   10                  15

Val Lys Leu Ser Cys Thr Ala Ser Gly Phe Asn Ile Lys Asp Thr Tyr
            20                  25                  30

Met His Trp Val Lys Gln Arg Pro Glu Gln Gly Leu Glu Trp Ile Gly
        35                  40                  45

Arg Ile Asp Pro Ala Asn Gly Asn Thr Lys Tyr Asp Pro Lys Phe Gln
    50                  55                  60

Gly Lys Ala Thr Ile Thr Ala Asp Thr Ser Ser Asn Thr Ala Tyr Leu
65                  70                  75                  80

Gln Leu Ser Ser Leu Thr Ser Glu Asp Thr Ala Val Tyr Tyr Cys Ala
                85                  90                  95

Arg Trp Asp Trp Tyr Phe Asp Val Trp Gly Gly Thr Thr Val Thr
            100                 105                 110

Val

<210> SEQ ID NO 19
<211> LENGTH: 118
<212> TYPE: PRT
<213> ORGANISM: Mus musculus

<400> SEQUENCE: 19

Ser Glu Val Gln Leu Gln Gln Ser Gly Ala Glu Leu Val Lys Pro Gly
1               5                   10                  15

Ala Ser Val Lys Leu Ser Cys Thr Ala Ser Gly Phe Asn Ile Lys Asp
            20                  25                  30

Thr Tyr Ile His Trp Val Lys Gln Arg Pro Glu Gln Gly Leu Glu Trp
        35                  40                  45

Ile Gly Arg Ile Asp Pro Ala Ile Gly Asn Thr Lys Tyr Asp Pro Lys
    50                  55                  60

Phe Gln Gly Lys Ala Thr Ile Thr Ala Asp Thr Ser Ser Asn Thr Ala
65                  70                  75                  80

```
Tyr Leu Gln Leu Ser Ser Leu Thr Ser Glu Asp Thr Ala Val Tyr Tyr
            85                  90                  95

Cys Ser Arg Gly Ile Thr Pro Tyr Tyr Ala Ile Asp Tyr Trp Gly Gln
            100                 105                 110

Gly Thr Ser Val Thr Val
            115

<210> SEQ ID NO 20
<211> LENGTH: 112
<212> TYPE: PRT
<213> ORGANISM: Mus musculus

<400> SEQUENCE: 20

Val Gln Leu Gln Gln Ser Gly Ala Glu Leu Val Lys Pro Gly Ala Ser
1               5                   10                  15

Val Lys Leu Ser Cys Thr Ala Ser Gly Phe Asn Ile Lys Asp Thr Tyr
            20                  25                  30

Met His Trp Val Lys Gln Arg Pro Glu Gln Gly Leu Glu Trp Ile Gly
        35                  40                  45

Arg Ile Asp Pro Ala Asn Gly Asn Thr Lys Tyr Asp Pro Lys Phe Gln
    50                  55                  60

Gly Lys Ala Thr Ile Thr Ala Asp Thr Ser Ser Asn Thr Ala Tyr Leu
65                  70                  75                  80

Gln Leu Ser Ser Leu Thr Ser Glu Asp Thr Ala Val Tyr Tyr Cys Val
                85                  90                  95

Ser Ser Tyr Ala Met Asp Tyr Trp Gly Gln Gly Thr Ser Val Thr Val
            100                 105                 110

<210> SEQ ID NO 21
<211> LENGTH: 116
<212> TYPE: PRT
<213> ORGANISM: Mus musculus

<400> SEQUENCE: 21

Val Gln Leu Gln Gln Ser Gly Ala Glu Leu Val Lys Pro Gly Ala Ser
1               5                   10                  15

Val Lys Leu Ser Cys Ser Ala Ser Gly Phe Asn Ile Lys Asp Thr Tyr
            20                  25                  30

Met His Trp Val Lys Gln Arg Pro Glu Gln Gly Leu Glu Trp Ile Gly
        35                  40                  45

Arg Ile Asp Pro Ala Asn Gly Asn Thr Lys Tyr Asp Pro Lys Phe Gln
    50                  55                  60

Gly Lys Ala Thr Ile Thr Ala Asp Thr Ser Ser Asn Thr Ala Tyr Leu
65                  70                  75                  80

Gln Leu Ser Ser Leu Thr Ser Glu Asp Thr Ala Val Tyr Tyr Cys Ala
                85                  90                  95

Arg Trp Leu Leu Arg Tyr Tyr Ala Met Asp Tyr Trp Gly Gln Gly Thr
            100                 105                 110

Ser Val Thr Val
            115

<210> SEQ ID NO 22
<211> LENGTH: 117
<212> TYPE: PRT
<213> ORGANISM: Mus musculus
```

<400> SEQUENCE: 22

Ser Glu Val Gln Leu Gln Gln Ser Gly Ala Glu Leu Val Lys Pro Gly
1               5                   10                  15
Ala Ser Val Lys Leu Ser Cys Thr Ala Ser Gly Phe Asn Ile Lys Asp
            20                  25                  30
Thr Tyr Met His Trp Val Lys Gln Arg Pro Lys Gln Gly Leu Glu Trp
        35                  40                  45
Ile Gly Arg Ile Asp Pro Ala Asn Gly Tyr Thr Glu Tyr Asp Pro Lys
    50                  55                  60
Phe Gln Gly Lys Ala Thr Ile Thr Ala Asp Thr Ser Thr Asn Thr Ala
65                  70                  75                  80
Tyr Leu Gln Leu Ser Ser Leu Thr Ser Glu Asp Thr Ala Val Tyr Tyr
                85                  90                  95
Cys Thr Gly Gly Asn Tyr Ala Tyr Gly Met Asp Tyr Trp Gly Gln Gly
            100                 105                 110
Thr Ser Val Thr Val
            115

<210> SEQ ID NO 23
<211> LENGTH: 114
<212> TYPE: PRT
<213> ORGANISM: Artificial Sequence
<220> FEATURE:
<223> OTHER INFORMATION: synthetic construct

<400> SEQUENCE: 23

Asp Ile Val Leu Thr Gln Ser Pro Ser Ser Leu Thr Val Thr Ala Gly
1               5                   10                  15
Glu Lys Val Thr Met Ser Cys Lys Ser Ser Gln Ser Leu Leu Asn Ser
            20                  25                  30
Gly Asn Gln Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Gln Asn
                85                  90                  95
Asp Tyr Ser Tyr Pro Phe Thr Phe Gly Ser Gly Thr Lys Leu Glu Ile
            100                 105                 110
Lys Arg

<210> SEQ ID NO 24
<211> LENGTH: 115
<212> TYPE: PRT
<213> ORGANISM: Mus musculus

<400> SEQUENCE: 24

Asp Ile Glu Leu Thr Gln Ser Pro Ser Ser Leu Thr Val Thr Ala Gly
1               5                   10                  15
Glu Arg Val Thr Met Ser Cys Lys Ser Ser Gln Ser Leu Leu Asn Ser
            20                  25                  30
Gly His Gln Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60

```
Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Phe Pro Tyr Pro Phe Gly Gly Gly Thr Lys Leu Glu Ile
            100                 105                 110

Lys Arg Ala
        115

<210> SEQ ID NO 25
<211> LENGTH: 114
<212> TYPE: PRT
<213> ORGANISM: Artificial Sequence
<220> FEATURE:
<223> OTHER INFORMATION: synthetic construct

<400> SEQUENCE: 25

Asp Ile Glu Leu Thr Gln Ser Pro Ser Ser Leu Thr Val Thr Ala Gly
  1               5                  10                  15

Glu Lys Val Thr Met Asn Cys Lys Ser Ser Gln Ser Leu Leu Asn Ser
                 20                  25                  30

Arg Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Val Tyr Pro Leu Thr Phe Gly Ala Gly Thr Lys Leu Glu Ile
            100                 105                 110

Lys Arg

<210> SEQ ID NO 26
<211> LENGTH: 114
<212> TYPE: PRT
<213> ORGANISM: Mus musculus

<400> SEQUENCE: 26

Asp Ile Glu Leu Thr Gln Ser Pro Ser Ser Leu Thr Val Thr Ala Gly
  1               5                  10                  15

Glu Lys Val Thr Met Asn Cys Lys Ser Ser Gln Ser Leu Leu Asn Ser
                 20                  25                  30

Arg Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Val Tyr Pro Leu Thr Phe Gly Ala Gly Thr Lys Leu Glu Ile
            100                 105                 110

Lys Arg
```

<210> SEQ ID NO 27
<211> LENGTH: 114
<212> TYPE: PRT
<213> ORGANISM: Mus musculus

<400> SEQUENCE: 27

Asp Ile Val Met Thr Gln Ser Pro Ser Ser Leu Thr Val Thr Ala Gly
1               5                   10                  15

Glu Lys Val Thr Met Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Arg

<210> SEQ ID NO 28
<211> LENGTH: 115
<212> TYPE: PRT
<213> ORGANISM: Mus musculus

<400> SEQUENCE: 28

Asp Ile Gln Met Thr Gln Ser Thr Ser Ser Leu Thr Val Thr Ala Gly
1               5                   10                  15

Glu Lys Val Thr Met Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Arg Ala
        115

<210> SEQ ID NO 29
<211> LENGTH: 114
<212> TYPE: PRT
<213> ORGANISM: Mus musculus

<400> SEQUENCE: 29

Asp Ile Val Met Thr Gln Ser Pro Ser Ser Leu Thr Val Thr Ala Gly
1               5                   10                  15

Glu Lys Val Thr Met Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

-continued

```
Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ser Gly Thr Lys Leu Glu Ile
            100                 105                 110

Lys Arg

<210> SEQ ID NO 30
<211> LENGTH: 115
<212> TYPE: PRT
<213> ORGANISM: Mus musculus

<400> SEQUENCE: 30

Asp Ile Val Met Thr Gln Ser Pro Ser Ser Leu Ser Val Ser Ala Gly
  1               5                  10                  15

Glu Arg Val Thr Met Ser Cys Lys Ser Gln Ser Leu Leu Asn Ser
                 20                  25                  30

Gly Asn Gln Lys Asn Phe Leu Ala Trp Tyr Gln Gln Lys Pro Gly Gln
             35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp His Ser Tyr Pro Leu Thr Phe Gly Ala Gly Thr Lys Leu Glu Ile
            100                 105                 110

Lys Arg Ala
        115

<210> SEQ ID NO 31
<211> LENGTH: 115
<212> TYPE: PRT
<213> ORGANISM: Artificial Sequence
<220> FEATURE:
<223> OTHER INFORMATION: synthetic construct

<400> SEQUENCE: 31

Asp Ile Val Met Thr Gln Ser Pro Ser Ser Leu Ser Val Ser Ala Gly
  1               5                  10                  15

Glu Arg Val Thr Met Ser Cys Lys Ser Gln Ser Leu Leu Asn Ser
                 20                  25                  30

Gly Asn Gln Lys Asn Phe Leu Ala Trp Tyr Gln Gln Lys Pro Gly Gln
             35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp His Ser Tyr Pro Leu Thr Phe Gly Ala Gly Thr Lys Leu Glu Leu
            100                 105                 110

Lys Arg Ala
        115
```

```
<210> SEQ ID NO 32
<211> LENGTH: 114
<212> TYPE: PRT
<213> ORGANISM: Mus musculus
<220> FEATURE:
<221> NAME/KEY: VARIANT
<222> LOCATION: 81
<223> OTHER INFORMATION: Xaa = Any Amino Acid

<400> SEQUENCE: 32

Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
             20                  25                  30

Gly Asn Gln Lys Asn Tyr Leu Thr Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Xaa Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Leu
             100                 105                 110

Lys Arg

<210> SEQ ID NO 33
<211> LENGTH: 14
<212> TYPE: PRT
<213> ORGANISM: coliphage M13

<400> SEQUENCE: 33

Met Lys Lys Leu Leu Phe Ala Ile Pro Leu Trp Pro Phe Tyr
 1               5                  10
```

METHOD FOR OBTAINING SINGLE CHAIN ANTIBODIES TO HUMAN INTERFERON α2B

BACKGROUND OF THE INVENTION

1. Field of the Invention

Embodiments of the invention relate to a bacterial high-expression system and its use for screening of recombinant clones from single chain (sc) antibody libraries and simultaneous isolation of the desired ScFv based upon the screening. Also disclosed are scFv antibodies to interferon α2b produced by the method.

2. Description of the Related Art

1. Single Chain Variable Fragment (scFv) Antibody

Antibodies hold a firm place in biological research and have an increasingly important role in medical and industrial applications. Antibodies are highly selective binding agents and can be generated against any substance by standard approaches. In particular, monoclonal antibodies provide homogenous antibodies of predefined specificity. Antibody fragments can be generated in *E. coli* that have the same affinity as the complete antibody. Methods for the generation of large repertoires of diverse antibody molecules in bacteria has been described (Hurse, et al. (1989) Science 246: 1275-1281).

The smallest portion containing an antigen-binding site is the variable fragments (Fv) of an antibody. There are variable fragments on both the light and heavy chains. In single chain Fv (scFv) the two antigen binding variable regions of the light and heavy chain (VH Fv and VL Fv) are artificially connected by a linker peptide, designated as single chain variable fragment or single chain antibody (Bird, et al. (1988) Science 242:423-426; Orlandi, et al (1989) Proc Natl Acad Sci USA 86:3833-3837; Clarkson et al., Nature 352: 624-628 (1991)). The antigen binding site is made up of the variable domains of light and heavy chains of a monoclonal antibody. Several investigations have shown that the Fv fragment has indeed the full intrinsic antigen binding affinity of one binding site of the whole antibody. To stabilize the association of the recombinant Fv fragments, the fragments were joined with a short peptide linker and expressed as a single polypeptide chain. A variety of linker peptides, generally of length 12-25 aa, were tested and did not disturb the proper folding of the VH and VL domains (Bird, et al. (1988) ibid; Huston et al (1988) Proc Natl Acad Sci: USA 85: 5879-5883).

A frequently used linker for scFv antibodies is (Gly4Ser)3, a single 15 amino acid peptide with 12 glycines and 3 serines that bridges the ~4.5 nm (theoretical distance 5.4 nm, Hudson P (1995) Structure and application of single-chain Fvs as diagnostic and therapeutic agents. In: H. Zola (ed), Monoclonal antibodies the second generation. BIOS Scientific Publishers Limited, Oxford, UK.) gap between the C terminus of one domain and the N terminus of the other and has a flexible structure with inhanced mobility (Huston, et al., (1988) ibid; Freund, et al (1993) FEBS Lett 320:97-100). This construction facilitates chain pairing and minimizes refoldings and aggregations encountered when the two chains are expressed individually.

ScFv antibodies have the following advantages:
1. ScFv antibodies overcome the problem of dissociation of VH and VL often encountered with Fv fragments.
2. ScFv antibodies provide immunologically active molecules of conveniently small size.
3. ScFv antibodies can be produced on a large scale by fermentation with high purity and at low cost.
4. ScFv antibodies can be easily genetically manipulated.

ScFv antibodies is a broad term and is used herein in its usual sense. In particular, the term ScFv includes scFv antibodies, recombinant phage display of scFv antibodies, dimeric forms of scFv antibodies, dimeric forms of scFv or miniantibodies, bi-specific scFv (diabodies) and multimeric ScFv forms.

Small scFv fragments are considered promising for medical and biological applications because of superior tissue penetration, absence of side reactions involving the constant domains, as well as engineering of fusion protins, such as scFv-coupled toxins, the creation of multivalent or bispecific proteins or Antibody directed enzyme prodrug therapy (ADEPT) (Syrigos, et al (1999) Anticancer Res 19:605-613).

2. Selection Strategies

The use of currently developed techniques such as phage display (Smith G P (1985) Science 228:1315-1317; Winter, et al. (1994) Annu Rev Immunol 12:433-455; Dunn I S (1996) Curr Opin Biotechnol 7:547-553), ribosome display (Mattheakis, et al. (1994) Proc Natl Acad Sci USA 91:9022-9026; Hanes, et al. (1997) Proc Natl Acad Sci USA 94:4937-4942), yeast surface display (Bader E T, et al. (1997) Nature Biotechnol 15:553-557) and bacterial display (Daugherty, et al. (1998) Protein Eng 11:825-832) for in vitro selection of molecular interactions under evolutionary pressure has provided a new perspective in antibody engineering. Phage display has been most widely used (Cortese, et al. (1996) Curr Opin Biotechnol 7:616-621; Hoogenboom, et al. (1998) Immunotechnology 4:1-20). Phage display relies on fusing the protein of interest to a minor coat protein of the phage, the gene3 protein (g3p). In phage display, a ligand (e.g. an antigen) is immobilized and a collection of binding proteins (e.g. antibodies) are displayed on the phage, that is, provided as a fusion with the g3p (McCafferty et al., Nature, 348: 552-554 (1990); Soderlind et al., Immunol. Reviews 130: 109-124 (1992); Winter, et al. (1994) Annu Rev Immunol 12:433-455). The general technique for filanentous phage display is described in U.S. Pat. No. 5,658,727. The essential trick is that the genetic information of the displayed protein is contained within the phage DNA in the same phage particle and thus, physically connected to the expressed protein.

Antibody phage display requires that a repertoire or library of immunoglobulin-encoding genes be cloned into the filamentous phage. The library is accomplished by amplifying the variable region of immunoglobulin fragments or germline V-genes. The PCR products are cloned into a filamentous phage to incorporate a heavy chain and a light chain variable region cDNA copy connected by a linker and expressed on the surface of the filamentous phages. The phages without binding ability will be removed by washing. The remaining phages are used to infect *E. coli* for their amplification. The selection procedure, the so-called panning, can be repeated with increasing stringency to select clones with the highest affinity (Mersmann, et al. (1998) J Immunol Methods 220: 51-58). Panning (as described by Parmley, et al. Gene 73: 305-318 (1988)) and is preferred because high titers of phage can be screened easily, quickly and in small volumes. Furthermore, this procedure can select minor antibody fragment species within the population which otherwise would have been undetectable and amplify them to achieve a substantially homogenous population.

Phage display technology has been applied in many fields within the biological and medical sciences for study of molecular interactions and especially in the generation of monoclonal antibodies. However, high costs and time-consuming processes involving several rounds of panning and phage rescue are an intrinsic problem of a phagemid-based display system. The disadvantage of this approach also is that the yield of antibodies obtained using secretion vectors is relatively low. In most cases it is possible to avoid several cycles of phage rescue after antigen-affinity selection procedures which simplifies detection when screening a large numbers of clones. Other methods for producing divers libraries of antibodies and screening for desirable binding specificities are described in U.S. Pat. Nos. 5,667,988 and 5,759,817. The enriched antibodies are also screened with additional detection techniques such as expression colony lift (Young, et al. (1983) Science 222: 778-782, incorporated herein by reference) or cell surface display (U.S. Pat. No. 5,866,344). Vectors for this purposes are described in U.S. Pat. No. 5,348, 867. Such methods are applicable for detection in situ of colonies expressing recombinant antibodies having the desired characteristics. Embodiments of the present invention are directed to the development of a bacterial expression system for simultaneous screening of large numbers of recombinant clones from preliminary selected antibody libraries. But in contrast to published protocols, after screening, the clones, which express the recombinant antibodies to desired antigen, can be directly used for large-scale production of the ScFvs.

3. Expression Strategies for ScFv in *Escherichia coli* a. Expression by Secretion

Embodiments of the invention address the need to find protein expression systems that are convenient and highly-productive for large-scale production. There are several ways to express antibody fragments in *E. coli* and there are some advantages common to all various approaches. But there is no single expression strategy for antibody fragments now. The choice depends very critically on the intended application, be it the mass production of a single antibody species, the rapid engineering of an antibody, its structure determination, the testing of many variants or the screening of libraries. Requirements will also differ for antibodies intended for human or animal use as opposed to those intended for in vitro research or industrial purposes only.

Many strategies and vector constructions have been used for the expression of antibody fragments in *E. coli*. One way to obtain ScFv in a biologically active form is functional expression by secretion. The secretion of the ScFv gives rise to native and functional antibody fragments, and leads to many of the attractive features of a bacterial expression system, notably the screening of binding activity without prior in vitro folding. The essence of the strategy is to reproduce in *E. coli* the normal folding and assembly pathway of antibodies within the eukaryotic cell. In antibody producing cells, the two chains are expressed separately as precursors with N-terminal signal sequences and separately transported to the lumen of the endoplasmic reticulum (ER). There, the signal sequences are cleaved by a membrane-bound signal peptidase. In the lumen of the ER, folding of the protein, disulfide bond formation and assembly of the complete antibody take place.

The main hypothesis in the design of the secretory expression system for antibody fragments was that protein transport to the periplasm of *E. coli* is functionally equivalent to the transport of a protein to the lumen of the ER. A system was designed that directs ScFv to the periplasm of the same *E. coli* cell. The main advantage of this secretory expression system is that it directly leads to an assembled functional product with correctly formed disulfide bonds without the need to refold the protein in vitro. Generally, the desired antibody fragment is fused to an amino acid sequence that includes the signals for localization to the outer membrane and for translocation across the outer membrane. The amino acid sequences responsible for localization and for translocation across the outer membrane may be derived either from the same bacterial protein or from different proteins of the same or different bacterial species or from some bacteriophages. A wide variety of signal peptides have been used successfully in *E. coli* for protein translocation to the periplasm. These include prokaryotic signal sequences, such as the *E. coli* signals PhoA (Denefle, et al. (1989) Gene 85:499-510), OmpA (Denefle et al., 1989, ibid; Ghrayeb, et al. (1984) EMBO J. 3:2437-2442; Goldstein, et al. (1990) J. Bacteriol. 172:1225-1231), OmpT (Johnson, et al. (1996) Protein Expression Purif. 7:104-113), LamB and OmpF (Hoffman, et al. (1985) Proc. Natl. Acad. Sci. USA 82:5107-5111), b-lactamase (Kadonaga, et al. (1984) J. Biol. Chem. 259:2149-2154), Pe1B from *Erwinia carotovora* (Better, et al. (1988) Science 240: 1041-1043; Lei, et al. (1987) J. Bacteriol. 169: 4379-4383), leader sequences cpVIII and cpVIII from M13 filamentous phage coat proteins. The disadvantage of this approach is that protein yield is relatively low in most cases reported (Skerra, A. (1993) Current Opinion in Immunology 5, 256-262; Raag, et al. (1995) FASEB Journal 9, 73-80), and this places certain limitations on the use of such systems for preparative obtaining of recombinant-antibodies. The present invention represents the development a bacteria high-expression system which can be used for large scale production of the ScFvs as inclusion bodies.

b. Cytoplasmic Expression

The second approach is to produce scFv or Fv as insoluble cytoplasmic inclusion bodies. This strategy was used in the first reports on expressing antibodies in *E. coli* (Boss et al (1984) Nucleus Acid Res 12: 3791-3806; Cabilly et al. (1984) Proc Natl Acad Sci USA 81: 3273-3277). All types of antibody fragments (Fab, Fv, ScFv) have been produced in this way (Bird, et al. (1988) Science 242:423-426; Huston et al (1988) Proc Natl Acad Sci: USA 85: 5879-5883; Field, et al. (1990) Protein Eng. 3: 641-647; Pantoliano et al (1991) Biochemistry 30: 10117-10125; Cheadle et al (1992). Mol Immunol 29: 21-30) and a variety of strains, plasmids and promoters have been used. The T7 system, as a particularly strong, but regulatable system, was found useful (Huston et al (1991) Methods Enzymol 203: 46-88, Freund, et al. (1993) FEBS Lett 320:97-100). For many years, expression systems which produced soluble secreted recombinant proteins were favored over systems which produced ScFv as inclusion bodies because of the difficulties encountered when refolding inclusion body proteins; however, careful examination of the folding conditions allowed researchers to find ways to refold disulphide bonded proteins with relatively high yields. The development of improved methods for refolding ScFvs would greatly enhance their availability and utility.

However, since inclusion bodies contain mis-folded proteins that lack biological activity, the expression of antibodies of interest cannot be monitored directly by functional assay. Embodiments of the present invention relate to development of a bacterial high-expression system which is useful for screening antibody libraries by direct functional assay. Linkage of overexpression and screening in the developed system is accomplished by the combination of targeting some ScFvs into the periplasm of bacterial cell to allow for convenient screening of the library member of interest and the formation of inclusion bodies in the cytoplasm. Periplasmic targeting is provided by the presence of a secretory leader peptide at the N-terminus. Formation of cytoplasmic inclusion bodies is provided by the presence of the strong promoter T7 in the expression vector.

Expression of single chain antibody fragments as inclusion bodies is advantageous due to the very high levels of enriched protein produced and the protection of the protein product from proteolytic degradation. In addition, when producing a recombinant product which can be toxic or lethal to the host cell, the inclusion body protects the host from toxic and/or lethal effects. ScFv proteins produced in inclusion bodies have been successfully refolded. Properly folded proteins can be produced from inclusion bodies using a variety of solubilization and refolding schemes (Rudolph, et al. (1996). FASEB J. 10, 49-56; Marston, et al. (1990). Methods Enzymol. 182, 264-276 which are incorporated herein by reference). But the key to a successful commercial refolding process lies in achieving high yields while refolding at high protein concentrations (De Bernardez Clark, E. (1998). Curr. Opin. Biotechnol. 9, 157-163). Embodiments of the present invention also include optimization of the refolding process for ScFv to human interferon a2b. The developed method is applicable for large-scale production of biologically active ScFv hexahistidine proteins in bacterial inclusion bodies.

SUMMARY OF THE INVENTION

Embodiments of the invention are directed to a method for selecting a desired single chain antibodies (ScFv) from a combinatorial antibody library which includes the steps of:
transforming E. coli cells with a vector which includes:
    a strong promoter;
    a sequence encoding a leader sequence for secretion to the E. coli periplasm; and
    ScFv inserts from the combinatorial antibody library;
screening the library in the transformed E. coli cells for the presence of the desired ScFv by expressing the ScFv in the bacterial periplasm;
selecting and amplifying a colony expressing the desired ScFv; and
purifying the desired ScFv from inclusion bodies of the selected colony.

In preferred embodiments of the invention, the combinatorial antibody library is a phage display library. More preferably, the phage display library undergoes preselection with one or more rounds of panning.

In preferred embodiments, the vector also includes an affinity tag and the ScFv is purified from the inclusion bodies by affinity chromatography.

In preferred embodiments, the screening step further includes the steps of:
incubating the E. coli cells on a Master Plate to form colonies;
replicating the colonies from the Master Plate on a solid support;
transferring the replica to a medium which includes IPTG;
incubating the colonies for expression of the desired ScFv in the periplasm;
lysing the colonies; and
screening the colonies for ability to bind to an antigen to the desired ScFv.

In preferred embodiments, the colonies are screened with the following steps:
reacting the antigen with the lysed colonies to form a first complex;
reacting the first complex with a polyclonal antibody to the antigen to form a second complex; and
reacting the second complex with a second antibody for detecting the presence of the ScFv.

Preferably, the solid support is a multiwell plate, a slide, a petri dish or a membrane. More preferably, the membrane is a nitrocellulose membrane.

In preferred embodiments, the E. coli cells encode a T7 RNA polymerase and the strong promoter is a T7 promoter.

Another embodiment of the invention is directed to a method for recovery of a ScFv antibody from E. coli inclusion bodies in biologically active form which includes the steps of:
solubilizing the inclusion bodies in a detergent to release the ScFv antibody;
oxidizing the released ScFv antibody to form disulfide bonds;
removing the detergent;
precipitating the oxidized ScFv antibodies;
dissolving the precipitated ScFv antibodies in a denaturing solution;
immobilizing the ScFv antibodies on a solid support;
renaturing ScFv antibodies on the solid support; and
eluting the ScFv antibodies in biologically active form.

Preferably, the ScFv antibody is an interferon α-2b antibody. In preferred embodiments, the detergent is N-lauroyl-sarcosine solution. In preferred embodiments, the oxidation takes place in the presence of a $Cu^{2+}$ catalyst. In preferred embodiments, the detergent is removed by butanol extraction. Preferably, the precipitation is by centrifugation. In preferred embodiments, the denaturing solution is a buffered urea solution. In preferred embodiments, the renaturation is performed with a linear phosphate gradient. Preferably, the solid support is Ni-NTA agarose.

Another embodiment of the invention is directed to an isolated nucleic acid for ScFv 17 (IN) having the sequence as shown in SEQ ID NO: 1.

Another embodiment of the invention is directed to an isolated ScFv 17 (IFN) protein having the sequence shown in SEQ ID NO: 2.

Another embodiment of the invention is directed to an isolated ScFv17 VH sequence having the amino acid sequence shown in FIG. 9 (SEQ ID NO:3).

Another embodiment of the invention is directed to an isolated ScFv17 VL sequence having the amino acid sequence shown in FIG. 9 (SEQ ID NO:4).

Another embodiment of the invention is directed to isolated oligonucleotides for introduction of a leader peptide into a vector which have the sequences shown in SEQ ID NOS: 5 and 6.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIG. 1 shows screening of the recombinant clones in the pET-expression system. The library was preliminary selected by two rounds of phage display. A—E. coli colonies before screening (master plate), B—colony dot blot.

FIG. 2 Dot blot illustrates the specificity and sensitivity of the screening method. A Dot blot colonies grown with addition of IPTG. B. Dot blot colonies grown without addition IPTG. In negative control (C) filter was not coated with antigen.

(IFN) induced for 9 h with 1 mM IPTG. Lane 2, total cell extract from uninduced BL21(DE3) cells carrying plasmid pET-PLScFv17 (IN). Lane 3, soluble fraction from induced cells. Lane 4, soluble fraction from uninduced cells. Lane 5, insoluble fraction from induced cells. Lane 6, insoluble fraction from uninduced cells. 5 μl of culture suspension were loaded on each lane.

Figure 4:
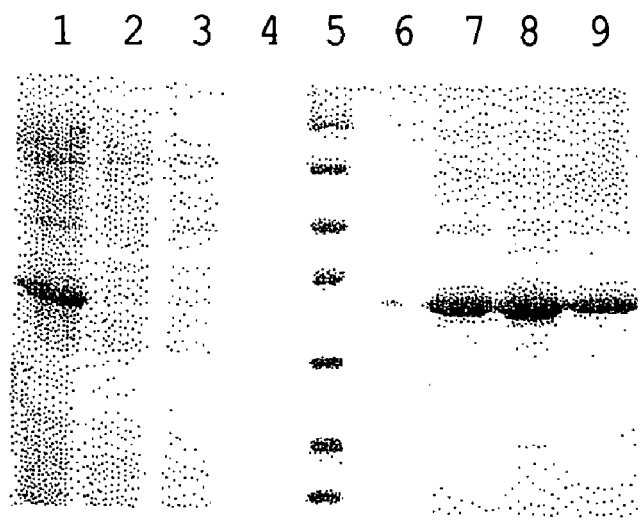

FIG. 4 SDS-PAGE analysis. Purification of ScFv under denaturing conditions from inclusion bodies by IMAC. Lane 1, total cell extract from BL21(DE3) cells carrying plasmid pET-PLScFv 17 (IFN) induced for 9 h with 1 mM IPTG. Lane 2, flow through. Lanes 3-4, PBS wash. Lane 5, MW standards 116, 66, 45, 35, 25, 18.4, 14.4 kDa. Lanes 6-9, eluted ScFv.

Figure 5:
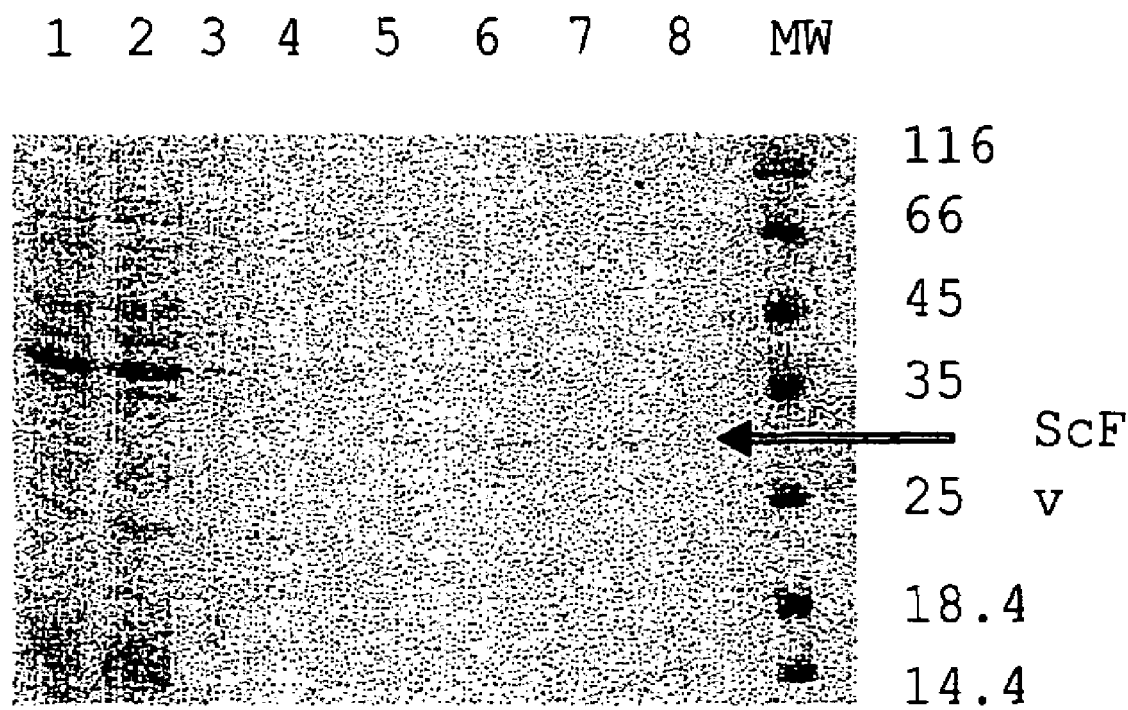

FIG. 5 SDS-PAGE analysis. Purification of ScFv to human interferon a2b under native conditions from *E. coli* periplasm by IMAC. Lane 1, periplasmic extract. Lane 2, proteins that did not bind to the Ni-NTA resin. Lanes 3-4, PBS wash. Lanes 5-8, eluted ScFv.

FIG. 6 shows the nucleotide sequence of the ScFv 17 (IFN) gene (SEQ ID NO:1).

FIG. 7 shows the amino acid sequence of the ScFv 17 (IFN) gene (SEQ ID NO: 2).

FIG. 8 shows the ScFv17 (IFN) building blocks (SEQ ID NO: 1).

FIG. 9 shows amino acid sequences of the VH (SEQ ID NO: 3) and VL (SEQ ID NO: 4) domains of the ScFv 17(IFN) (CDR: complementary determining regions).

FIG. 10 shows the sequence alignment of VH ScFv 17(IFN) with the GentPept protein database.

FIG. 11 shows the sequence alignment of VL ScFv 17(IFN) with the GentPept protein database.

Figure 12:
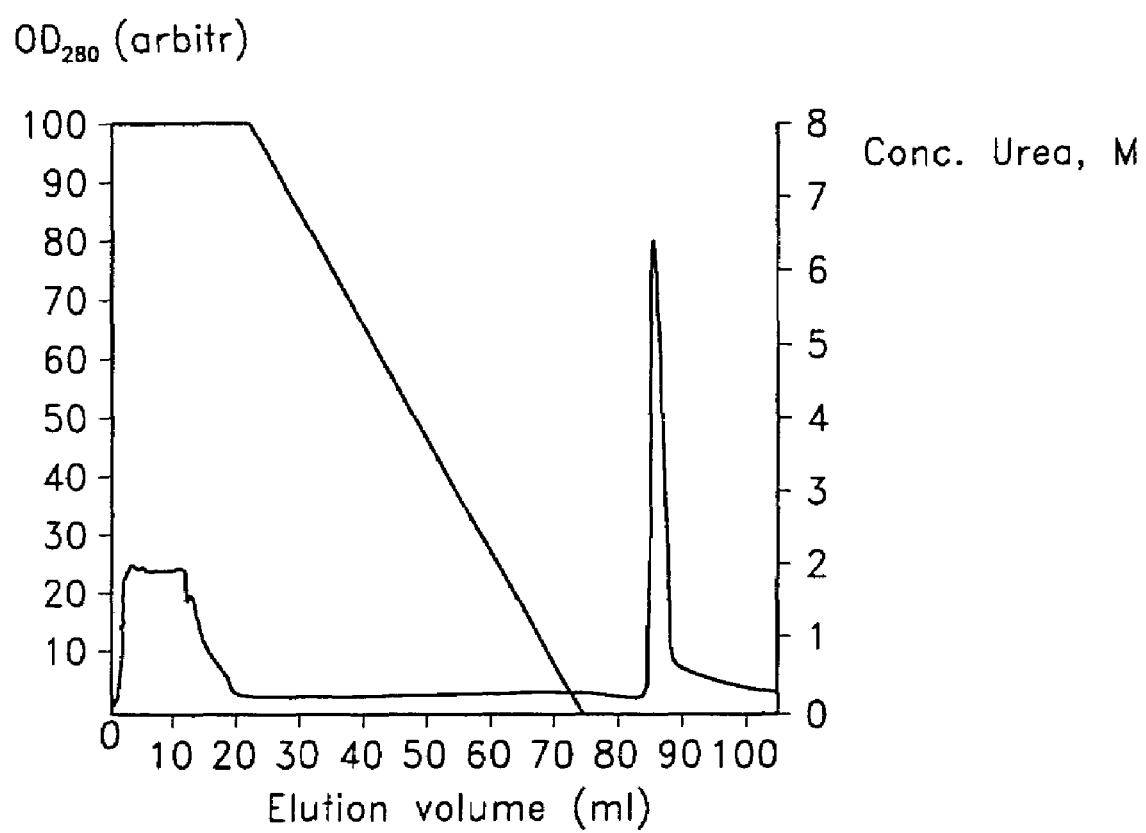

FIG. 12 shows the elution profile of refolded ScFv by IMAC after air oxidation of SH groups.

Figure 13:
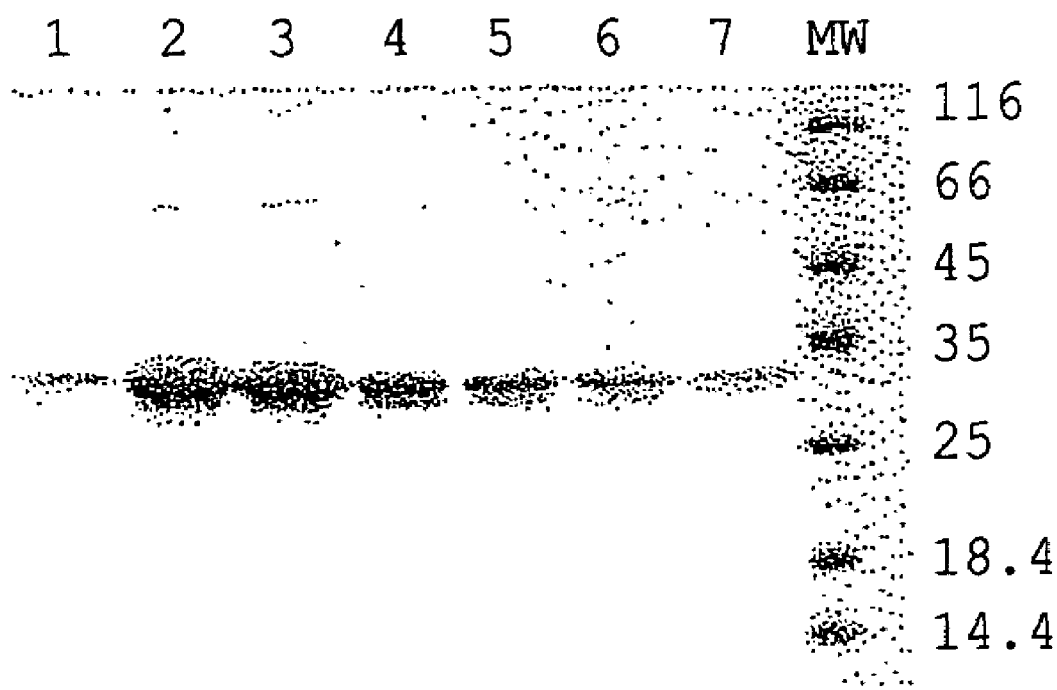

FIG. 13 shows protein fractions obtaining by imidazole elution of the refolded ScFv 17 (IFN) from Ni-NTA Agarose. A coomassie-stained SDS gel is shown. Lanes 1-7: purified and refolded inclusion bodies recovered from the column by 0.25 M imidazole. 1-10 μg protein was loaded in each lane of the 12% SDS-polyacrylamide gel.

Figure 14:
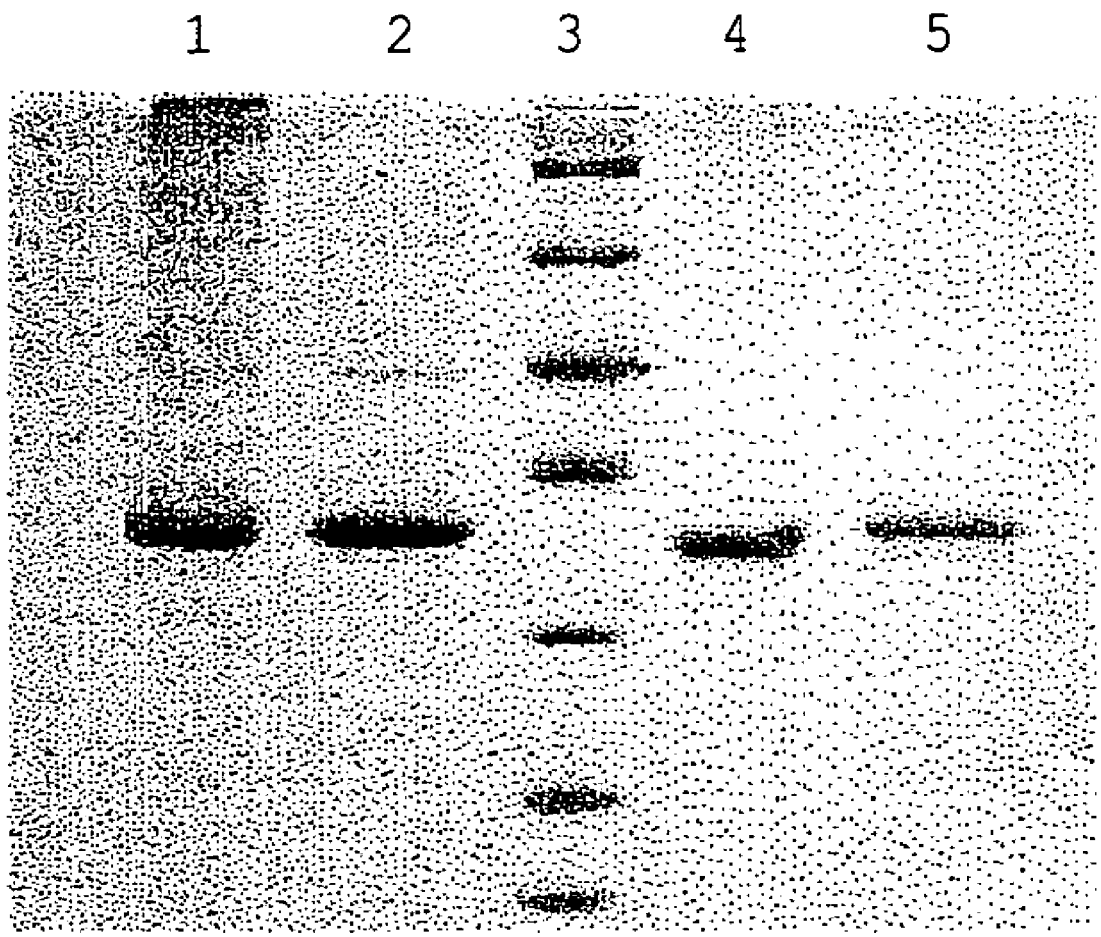

FIG. 14 illustrates the SDS-PAGE analysis for determination of disulfide bond formation in ScFv after refolding. Lanes 1-2, inclusion bodies before oxidation. Lanes 4-5 purified and refolded inclusion bodies recovered from the column by 0.25 M imidazole. Samples in lanes 1, 4 were run non-reduced, lanes 2,5—reduced. Lane 3, MW standards: 116, 66, 45, 35, 25, 18.4, 14.4 kDa.

Figure 15:
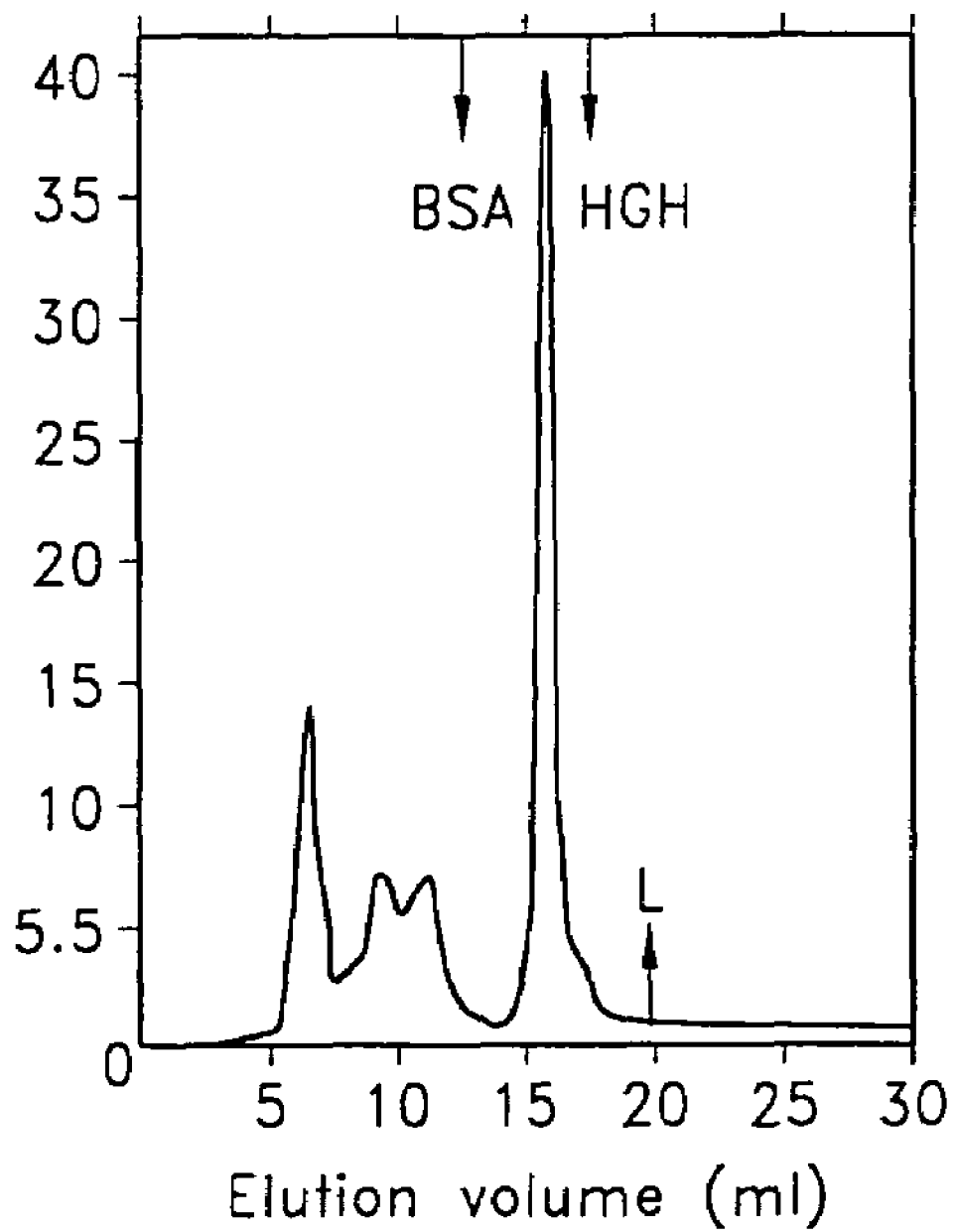

FIG. 15 shows the analytical gel filtration elution profile of the refolded ScFv. Gel filtration standards: BSA (bovine serum albumin), 68 kD; HGH (human growth hormone); 22 kDa, L (lysozyme) 14.4 kDa.

Figure 16:

FIG. 16 shows the specific interferon binding capacity of refolded matrix-immobilized ScFv (IFN). Lane 1, interferon loaded on column which contained refolded ScFvs. Lane 2, interferon that did not bind to the refolded ScFv. Lane 3, MW 116, 66, 45, 35, 25, 18.4, 14.4 kDa. Lanes 4-7—protein complexes released from the Ni-NTA column by 0.25 M imidazole.

Figure 17:
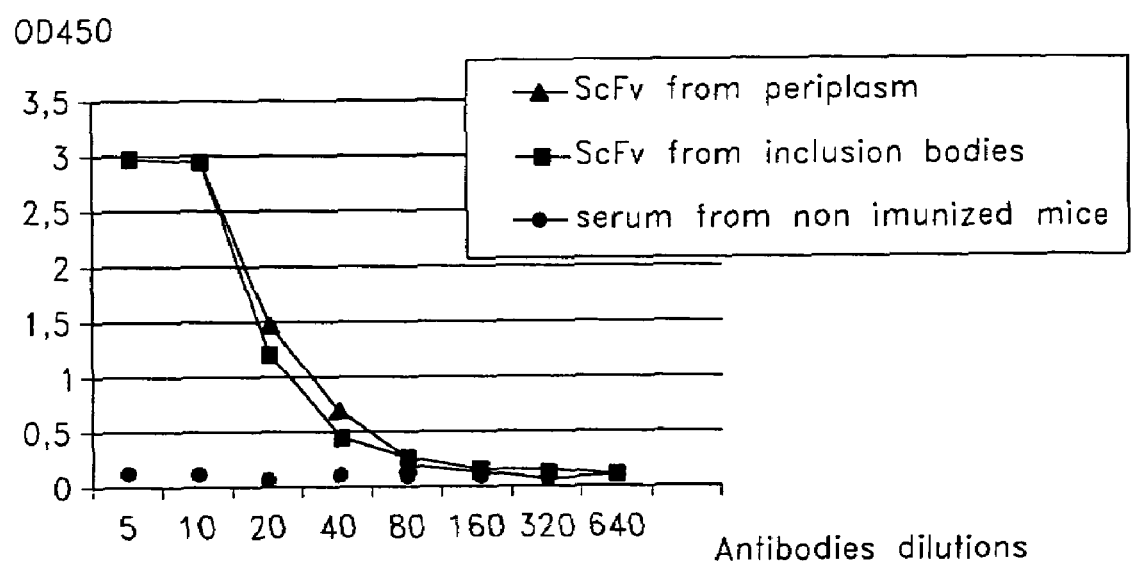

FIG. 17 illustrates ELISA results showing the comparison of the interferon binding activity of refolded ScFv (IFN) and ScFv (IFN) obtained from periplasm.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

1. System for High-level Expression and Simultaneous Screening of Large Numbers of Recombinant Antibody Clones from Combinatorial Antibody Libraries with Preliminary Selection by Phage Display One embodiment of the invention is directed to the development of a high expression system for production of ScFv to human interferon a2b. For maximized total ScFv production we used the vector plasmid pET 24a (+), containing the T7 promoter, with bacterial strain BL21 (DE3) (Novagene, USA), which encodes the T7 RNA polymerase in the chromosome under control of the lac promoter (Studier, et al. J. Mol. Biol. 189, 113-130). The T7 RNA polymerase elongates polypeptide chains approx. 5-fold faster than the RNA polymerase of *E. coli*. However, any system may be used which employs a strong promoter such as T7.

Other examples of strong promoters which may be used include promoter sequences derived from sugar metabolizing enzymes, such as galactose, lactose (lac) (Chang et al. (1977) Nature 198:1056), and maltose. Additional examples include promoter sequences derived from biosynthetic enzymes such as tryptophan (trp) (Goeddel et al. (1980) Nuc. Acids Res. 8:4057; Yelverton et al. (1981) Nucl. Acids Res. 9:731; U.S. Pat. No. 4,738,921; EPO Publ. Nos. 036 776 and 121 775). The b-lactamase (bla) promoter system (Weissmann (1981) "The cloning of interferon and other mistakes." In Interferon 3 (ed. I. Gresser)). Bacteriophage lambda PL (Shimatake et al. (1981) Nature 292:128) and T5 (U.S. Pat. No. 4,689,406) promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac promoter is a hybrid trp-lac promoter comprised of both trp promoter and lac operon sequences that is regulated by the repressor (Amann et al. (1983) Gene 25:167; de Boer et al. (1983) Proc. Natl. Acad. Sci. 80:21). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system.

In another embodiment of the invention a hybrid ScFv protein is constructed carrying the sequence MKKLLFAIPL-WPFY (GenBank Accession NC_003287; SEQ ID NO: 34) at the N-terminus for secretion and a hexahistidine sequence at the C-terminus (6 His Tag) which allows selective immobilization of the single chain antibodies on a Ni-NTA matrix. The immobilized single chain antibodies may then be renatured while on the solid support using a urea gradient. The refolded and purified protein is eluted under defined conditions. Other protein tags may also be used to provide an affinity for the column material. Such tags include, not are not limited to tagging with biotin, Flag-epitope or c-myc epitope or HA-tag, GST, MBP, Thioredoxin, β-Galactosidase, VSV-Glycoprotein, calmodulin binding protein, or any metal affinity tag such as the 6× His tag used herein. Preferably, the fusion partner does not change the binding properties of the ScFv. The affinity tag(s) may be fused at either the NH$_2$— or COOH— termini or at both termini simultaneously.

This N-terminal sequence used in preferred embodiments is the natural secretory leader peptide from gene III structural protein of coliphage M13. The use of this leader peptide provides good secondary structure in the mRNA transcript. Other secretory leader peptides may be used including ompA, ompF, ompT, LamB, b-lactamase, cp VIII from M13, pelB, malE or phoA signal peptides or leader sequences. The 5'-terminus of the mRNA should not interfere with the AUG translation initiation codon and/or ribosome-binding site and it should not hamper effective translation initiation.

As the His Tag at the C-terminus of the antibody fragments is compatible with transport through the *E. coli* membrane and folding (Lindner P., et al. Methods: A Companion to Methods in Enzymology 4, 41-56 (1992)), some ScFv-molecules during protein overproduction can be secreted to the periplasm. Expression of the ScFvs with desired specificity can be monitored from *E. coli* colonies directly by functional assay (colony blot). This principle underlies routine screening of recombinants developed by us. A replica of clones on nitrocellulose membrane is made from a Petri dish containing bacterial colonies. The membrane is placed on agar medium with IPTG. Expressed bacterial proteins (including ScFv secreted into periplasm) are lysed on the nitrocellulose membrane by freezing-thawing. The immobilized recombinant antibodies are screened for their ability to bind interferon. Clones which effectively bind interferon are detected with interferon polyclonal mouse antibody and a secondary antibody to detect the formation of immune complexes. Means to quantitate the extent of binding include colorimetric assays as well as radioimmunoassay. For example, alkaline phosphatase conjugated secondary antibody or secondary antibodies labeled with other enzymes (HRP) or dyes (fluorescent etc) may be used. In preferred embodiments, HRP/antimouse antibodies were used to detect the formation of immune complexes. This approach provides high specificity and sensitivity of reaction. This is achieved due to use of purified interferon polyclonal antibody from an immunized mouse. This approach is applicable for simultaneous screening of large numbers of recombinant clones from preliminary selected antibody libraries. In some cases, due to the large number of colonies that can be simultaneously screened, it may be possible to completely circumvent phage rescue and antigen-affinity selection procedures normally used in the identification of positive clones (especially those originating from a hybridoma source).

In another embodiment, using this secretion vector with a strong promoter permits transport of the soluble ScFv to the periplasm and cytoplasmic inclusion bodies simultaneously in the same bacterial cell. Besides overexpression, the T7 system provides N-terminal sequences for effective translation of ScFv RNA. The target protein accumulates as inclusion bodies at the level of a few grams per liter of bacterial suspension. Such a system is especially attractive for fast screening of recombinants from pre-selected antibody libraries with direct use of the clones which produced the antibodies to the target antigen for large-scale production ScFv from inclusion bodies.

2. Refolding of the ScFv to Human Interferon a2b

Several methods, including dilution, dialysis, diafiltration, gel filtration and immobilization on a solid support, can be employed to remove or decrease the levels of excess denaturing and reducing agents, allowing proteins to renature. Preferred embodiments of the present invention, show that fully active ScFvs to interferon a2b were renatured from cytoplasmic inclusion bodies in relatively high yield. In preferred embodiments, the refolding method was based on the reagent system described in methods for correct disulfide pairing in detergent solution (Kurucz, et al. (1995) Mol. Immunol. 32, 1443-1452) and Ni-NTA-assisted refolding (Holzinger, et al. (1996) Bio Techniques 20, 804-808) with some modifications. One advantage of the disclosed method which is in striking contrast to the prior art methods, is that we can refold the single chain antibodies at a high protein concentration without adding large tags (such as CBD) which must then be removed from ScFv by proteolytic digestion after refolding (Berdichevsky Y, Lamed R et al. Matrix-assisted refolding of single-chain Fv-cellulose binding domain fusion proteins: Protein Expression and Purification 17, 249-259 (1999)). Moreover, the protein can be obtained at 96% and higher purity after refolding. The refolding protocol is simple and based on cheap available materials.

Many proteins that are insoluble when refolded in solution can be successfully refolded while immobilized on the Ni-NTA matrix by C- or N-terminal 6-histidine tail, i.e., 6-His Tag. Immobilizing one end of the protein during renaturation appears to prevent intermolecular interactions, and aggregate formation. Renaturation using a linear urea gradient, which may be generated manually or using FPLC equipment, may be performed over a period of time, typically 1.5-2 h. Nevertheless, this approach may not be directly applicable to refolding of disulfide-bonded proteins, such as ScFv. In some embodiments, the disulfide formation is first kinetically catalyzed. Refolding of antibodies is not principally different from that of other disulfide containing proteins. In the case of ScFv obtained from inclusion bodies, renaturation buffer promotes disulphide bond formation (oxidation) before immobilization.

Recently it was shown that in vitro folding of recombinant single chain Fv proteins is markedly facilitated when disulfide bonds are formed in detergent solution, such as sodium lauroylsarcosine (Kurucz et al., 1995, ibid). The crucial aspect of the procedure is that ScFvs, when solubilized in detergent solutions, quantitatively form correctly paired disulfide bonds upon oxidation in air. Although the detergent greatly facilitated correct disulfide bond formation, removal of detergent presents a formidable problem. In preferred embodiments, the detergent is removed using selective precipitation of ScFvs by butanol extraction. After precipitation, the protein pellet which contained denatured ScFvs with correctly paired disulfide bonds can be redissolved in 8M urea solution and successfully refolded on the Ni-NTA matrix using a linear urea gradient. Upon removal of the urea, the ScFvs adopted native structures in high yields, aided by correctly paired disulfide bonds. Linear removal of the denaturant by FPLC equipment facilitates the refolding of the protein into the native state. The refolded protein can be released from NI-NTA matrix under mild conditions. Preferred embodiments of the invention specifically include optimization of a refolding process which is particularly applicable to large-scale production of biologically active ScFv-6 His proteins from bacterial inclusion bodies.

EXAMPLES

The following examples are illustrative of the invention and are not intended to limit the scope of the invention.

Example 1

Construction, Expression and Selection of Antibody Fragments on the Surface of M13

Mice Immunization

This example shows the synthesis of a diverse population of heavy (VH) and light (VL) chain antibody fragments from splenocytes and their enrichment by panning. Recombinant human interferon was obtained from PRSC "Biotechnolog". For immunization with interferon a2b, tree mice (BALB/c female, 2-month age, 18-20 g weight) were used. Immunization was performed 3 times by intraperitonial injection with an interval of 14 days, introducing 50 µg of interferon per mouse each time. The first administration was made with complete Freund's adjuvant. The second administration was with incomplete Freund's adjuvant. The third administration was without adjuvant (booster). In 14 days after finishing the immunization cycle, blood sera from the animals were tested by ELISA. Titer of the specific antibodies was 1:800-1:1600.

Isolation of mRNA

Total RNA was isolated from spleens of the tree mice immunized as described above using an RNA Extraction Kit (Pharmacia) as recommended by the manufacturer. Briefly, immediately after removing spleens from the mice, the tissue was homogenized in Extraction Buffer, which contains guanidinum thiocyanate (GTC). Cellular debris was removed by centrifugation, and the supernatant was passed through a syringe needle to shear chromosomal DNA. The extract was then loaded onto a "cushion" of CsTFA solution and centrifuged at 125 000 g for 16 hours at 15° C. Following aspiration of the supernatant, the RNA pellet was recovered and redissolved in TE buffer (10 mM Tris-HCL, pH 7.5, 1 mM EDTA).

Poly A RNA for use in first strand cDNA synthesis was prepared from the above isolated total RNA using a mRNA Purification Kit (Pharmacia) as recommended by the manufacturer. The basic methodology has been described by Sambrook, J., Fritsch, E. F. and Maniatis, T., Molecular cloning: A laboratory Manual, Cold Spring Harbor Laboratory, Second edition (1989), which is incorporated herein by reference. Briefly, one half of the total RNA isolated from mice spleens prepared as described above was first heat-denatured at 65° C., then adjusted to an appropriate salt concentration (0.5 M NaCl) using sample buffer, and applied to the oligo(dT)-cellulose column. Unbound RNA was removed with several washes using high-salt buffer (0.5 M NaCl) followed by low-salt buffer (0.1 M NaCl). The poly(A)+ RNA was then recovered by elution with warm no-salt buffer. The washing and elution steps were all performed very quickly by low-speed centrifugation of the column.

PCR Amplification and Cloning of Antibody Variable Genes

All PCR reactions were performed by Mouse ScFv Module (Pharmacia Biotech) as recommended by the manufacturer. Briefly, in preparation for PCR amplification, mRNA was used as template for cDNA synthesis. First-strand cDNA synthesis was performed from mRNA primed with random hexamers. PCR amplification of VH and VL was performed with the light-chain primer mix for VL and the heavy-chain primer mix for VH, for 30 cycles of 94° C. for 1 min, 55° C. for 2 min and 72° C. for 1 min. This was followed by a single incubation at 72° C. for 10 min. PCR products were isolated from the other reaction components by electrophoresis in 1.5% agarose gel and amplified into a single chain with linker DNA encoding $(Gly_4Ser)_3$. In the second PCR the assembled ScFv DNA were amplified and restriction sites for Sfi1 and Not1 were added. The VH-linker-VL antibody constructs were cloned into the Sfi1 and Not1 sites of the phagemid vector, pCANTAB 5E. Ligation, electroporation and plating out of the cells were as described by Sambrook et al., 1989, ibid.

Rescue of Library from Spleen and Panning

The phage antibody repertoire above was selected for antibodies to IFN a2b. The repertoire was treated as follows in order to rescue phagemid particles. 50 ml 2YT-AG (2YT media supplemented with 100 µg/ml ampicillin and 2% glucose) in 50 ml centrifuge tubes was inoculated with approximately $3 \times 10^9$ cells from a glycerol stock (−70° C.) culture of the library. The culture was grown at 37° C. with good aeration until the OD600 nm reached 0.7 (approximately 2 hours). M13K07 helper phage (Pharmacia) was added to the culture to a multiplicity of infection (moi) of approximately 10 (assuming that an OD600 nm of 1 is equivalent to $5 \times 10^8$ cells per ml of culture). The culture was incubated stationary at 37° C. for 15 minutes followed by 60 minutes with light aeration (200 rpm) at the same temperature. The culture was centrifuged to pellet the cells. The cells were resuspended in 50 ml 2YT-AK (2YT media supplement with 100 µg/ml ampicillin and 50 µg/ml kanamycin) and the culture incubated overnight at 30° C. with good aeration (300 rpm). Phage particles were precipitated by 4% (w/v) polyethylene glycol 8000 and 3% (w/v) NaCl and maintained on ice for 30 min, followed by centrifugation (10 000 g for 15 min) at 4° C. Phage pellets were resuspended in PBS and used for subsequent two rounds of panning as described below.

The panning procedure was a modification of that originally described by Parmley, et al. Gene 73: 305-318 (1988) and Carlos F. et al. Proc. Natl. Acad. Sci. USA. Vol. 88, 7978-7981, 1991. Two wells of a microliter plate (Nunc) were coated overnight at 4° C. with 100 µl of 10 µg/ml interferon prepared in 0.1 M bicarbonate, pH 9.6. The wells were washed twice with water and blocked by completely filling the well with 3% (w/v) non-fat dry milk in PBS and incubating the plate at 37° C. for 1 hour. Blocking solution was shaken out, 100 µl of the phage library prepared above (typically 1011 pfu) was added to each well and the plate was incubated for 2 hours at 37° C. Phage was removed and the plate was washed once with water. Each well was then washed 10 times with TBS/Tween (50 mM Tris-HCl, pH 7.5, 150 mM NaCl, 0.05% Tween 20) over a period of 1 hour at room temperature—pipetted up and down to wash the well, each time allowing the well to remain completely filled with TBS/Tween between washings. The plate was washed once more with distilled water and adherent phages were eluted by the addition of 100 µl of elution buffer (0.1 M HCl adjusted to pH 2.2 with glycine, containing 1 mg/ml BSA) to each well and incubation at room temperature for 10 minutes. The elution buffer was pipetted up and down several times, removed and neutralized with 6 µl of 2M Tris base per 100 µl of elution buffer used. Eluted phages were used to infect 2 ml of fresh (OD600-0.6) *E. coli* TG1 cells and the culture was shaken at 37° C. for 60 min. The infected cells were plated onto SOBAG medium.

Example 2

Screening of Periplasm Expression Libraries in BL21 (DE3) Cells

This example describes how the periplasm secretion of the recombinant antibody libraries can be used to identify clones that specific bind to the human interferon a2b Preparation of pET-PLScFv (IFN)

A vector was prepared from plasmid pET-24a (+) containing a kanamycin resistance gene for clone selection, the T7 promoter and a terminator for efficient transcription (Novagene, USA). The vector was prepared by removal of a DNA fragment from the polylinker with an NdeI/Hind III digest. The DNA encoding the leader peptide and SfiI site was introduced by ligation of the annealed DNA adapter molecules to generate compatible "sticky" ends. The DNA after ligation was ethanol precipitated and electroporated into DH 10B cells (Novagene, USA). Double strand vector DNA containing leader sequence were isolated as described in Sambrook et al., 1989. This intermediate construction was named pET-PL. Annealing oligonucleotides PL1 and PL2 are shown below.

PL1 (+) (SEQ ID NO:5)
5'TATGAAAAAATTATTATTCGCAATTCCTTTAGTTGTTCCTTTCTATGC GGCCCAGCCGGCCA 3'

PL2 (-) (SEQ ID NO:6)
5'AGCTTGGCCGGCTGGGCCGCATAGAAAGGAACAACTAAAGGAATTGCG AATAATAATTTTTTCA 3'

All E. coli colonies from the second round selection (approx. $3 \times 10^4$) were scraped from the plates by flooding each plate with 2 ml of 2YT medium and total double strand plasmid DNA were isolated as described above. The ScFv genes from the enrichment antibody library were obtained by PCR from total plasmid DNA as template and oligonucleotides R1 and R2 as primers. The PCR conditions were as follows: for 30 cycles of 94° C. for 30 sec, 55° C. for 1 min and 72° C. for 1 min. This was followed by a single incubation a 72° C. for 10 min.

R1 (+)
5' CCATGATTACGCCAAGCTTTGGAGCC 3'    (SEQ ID NO:7)

R2 (-)
5' CGATCTAAAGTTTTGTCGTCTTTCC 3'    (SEQ ID NO:8)

Following amplification, the PCR product was restricted with SfiI and NotI and ligated into the pET-PL vector digested with the same two enzymes. Resulting constructions contained double stranded inserts of the ScFv from the enriched combinatorial antibody library with translation initiation codon followed by a leader sequence and a hexahistidine tag on the C-terminus and were named pET-PLScFv (IFN).

Affinity Purification of the Mice Antibodies to Interferon a2b

Polyclonal antibodies to interferon a2b were purified from immunized mice serum using interferon-Sepharose resin that was prepared according to the manufacturer's instructions from CNBr-Activated Sepharose 4 Fast Flow (Pharmacia). Chromatography experiments were performed in batch with some modifications as described in "Antibodies: A Laboratory Manual, Cold Spring Harbor Laboratory", 1989. The serum was diluted in PBS to a final protein concentration of 2-5 mg/ml and added to 50% IFN-Sepharose suspension in PBS (approx. 1:1). The suspension was mixed gently by shaking at 4° C. for 8-12 hours and precipitated by centrifugation at 1000 g for 1 min. The resin was washed several times with PBS by centrifugation as described above. Elution was performed 4 times with elution buffer (0.1 M glycine HCl, pH 2.3). Eluted fractions were immediately neutralized with 0.2 M NaOH and interferon-binding activity was determined by ELISA.

Colony Blot Assay

In order to assess the ability to screen large numbers of clones and evaluate the frequency of antigen binding clones in a combinatorial library enriched by two rounds of panning, approximately $2 \times 10^4$ colonies were screened and about 50% of the clones which bound interferon were identified (FIG. 1). FIG. 2 illustrates the specificity and sensitivity of the screening method.

E. coli BL21 (DE3) (Novagene, USA) cells were transformed with pET—PLScFv (IFN) as described by Sambrook et at., 1989, ibid. To achieve well-isolated colonies, several dilutions of E. coli were plated onto Porcine-AG plates (porcine containing 1.5% agar, 100 µg/ml ampicillin and 1% glucose). These plates were designed as master plates. The 1000-3000 colonies per standard Petri dish were found to be optimal for obtaining individual clones. Fresh nitrocellulose filters (Hybomd—C Extra, Pharmacia) were placed onto corresponding master plates and incubated for 3 minutes. Filters with E. coli cells were placed (colony-side up) onto the plate containing Porcine-AAG with 1 mM IPTG (Fermentas). The plates were inverted and incubated overnight at 30° C. After incubation the filters were briefly frozen at −30° C. and washed with washing buffer (PBS, pH 7.4 containing 0.05% Tween 20) until no cellular debris was visible. All subsequent washes were with wash buffer. The filters were transferred to blocking buffer (PBS containing 3% milk powder) and incubated with gentle shaking for 1 hour. Blocked filters were coated with interferon (10 µg/ml) diluted in blocking buffer at room temperature for 1 hour. After washes, the mouse polyclonal anti-interferon antibodies diluted in blocking buffer (5-10->g/ml) were added and filters were incubated for 1 hour at 37° C. The polyclonal antibodies bound to the interferon-ScFv complexes were detected with HRP-conjugated anti-mouse monoclonal antibodies (Pharmacia) diluted in blocking buffer at 1:1000. The calorimetric substrate 4-CN (Sigma) was used for color reaction development. The filters were transferred to distilled water to stop the reaction.

Example 3

Expression of the ScFv to Human Interferon a2b

This example shows high-level production of single chain antibodies to interferon a2b. Several IFN a2b specific antibodies were isolated from the screening. Individual colonies from Porcine-agar were used to inoculate 1 ml Porcine media supplemented with 50 µg/ml kanamycin and containing 2% glucose. The cultures were incubated at 30° C. overnight and 200 µl were used for inoculation to 2 ml fresh Porcine media. The cultures were grown at 37° C. with good aeration until the OD600 nm reached 1.0 and then centrifuged at 5000 rpm for 10 min. Each cell pellet was resuspended in 50 ml Porcine media containing 1 mM IPTG and incubated at 30° C. overnight. After incubation the pellets from a single colony were lysed in SDS loading buffer and subjected to SDS-PAGE. One colony that produced large amounts of protein (clone No. 17) as judged by Coomassie staining was chosen for further experiments. The isolate from this clone plasmid was named pET-PLScFv17 (IFN) and, the single chain antibodies expressed from this clone were named ScFv17 (IFN). For the large-scale production of ScFvs, this colony was grown and induced as described above in 50 ml.

Determining Protein Localization

All cellular fractions (soluble/insoluble cytoplasmic proteins and periplasmic proteins) were analyzed by SDS-PAGE to determine ScFv localization.

Figure 3:
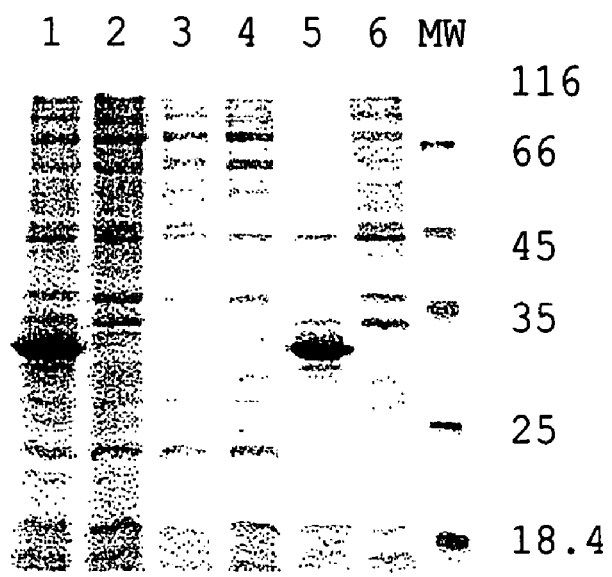
FIG. 3 illustrates SDS-PAGE analysis for determination of ScFv localization in E. coli cells. Lane 1, total cell extract from BL2I(DE3) cells carrying plasmid pET-PLScFv17

The majority of ScFv molecules were not able to traverse the bacterial membrane and were present in the cytoplasm as inclusion bodies (FIG. 3). But the ScFv yield that was expressed in the inclusion bodies was extremely high. The amount of ScFv expressed from BL21(DE3) was 30-50% of total bacterial proteins. To determine the accumulation level, ScFv were then purified under denaturing conditions from inclusion bodies by IMAC using Ni-NTA Agarose (Qiagen)

according to the manufacture's instructions. The results are shown in FIG. 4. Protein concentration was measured by absorbance at 280 nm. Molar absorptivity (Em) was calculated from amino acid sequence ScFv17 (IFN) by a Vector NTA computer program.

For verifying that soluble antibodies are also produced and to determine their accumulation levels, the periplasmic extract was prepared as described in Skerra, et al. Science 240, 1038 (1988). Briefly, periplasmic preparations were obtained by pelleting the cells from 20 ml at 5000 rpm for 10 min. The pellet was resuspended in 0.4 ml ice-cold 1×TES (0.2 M Tris-HCl (pH 8.0), 0.5 mM EDTA, 0.5 M sucrose) by vigorous shaking. 0.66 ml 1/5×TES was added. The cells were resuspended again and incubated on ice for 30 min. After centrifugation at 10 000 g for 10 min, the supernatant containing periplasmic proteins was loaded onto Ni-NTA Agarose (Qiagen) and purified, as recommended by the manufacturer. The ScFvs obtained from the periplasm are shown in FIG. 5. The functionality of the ScFvs eluted from the column was confirmed by ELISA. However, only a minor fraction of the total ScFvs were present in a soluble form in the bacterial periplasm (approx. 0.05 mg/l bacterial culture).

Template Preparation and Sequencing

Template was prepared for sequencing by inoculation of 1 ml overnight culture of DH 10B from a single colony (clone No. 17) into 100 ml of 2 YT medium containing 50 µg/ml kanamycin. The culture was incubated at 37° C. for 3-4 hours with shaking and then transferred to 50 ml centrifuge tubes. The bacteria were pelleted by centrifugation at 5000 g for 10 min and double stranded DNA containing ScFv was isolated from the cell pellet as described by Sambrook et al., 1989, ibid. The DNA sequence of the ScFv was determined using the Sanger dideoxy method described in Sanger, et al. Proc. Nat. Acad. Sci. USA. (1977) Vol. 74, 12: 5463-5467 using the AutoCycle™ Sequencing Kit following the protocol supplied by the manufacturer (Pharmacia).

PCR was performed for 30 cycles of 94° C. for 30 sec, 55° C. for 15 sec and 72° C. for 30 sec. This was followed by a single incubation at 72° C. for 10 min. The sequencing oligonucleotides used for priming (10 pmol each) are presented below.

```
                                              (SEQ ID NO:9)
5'-Cyanine-d[GGTTCAGGCGGAGGTGGCTCTGG]-3'

(SEQ ID NO:10)
5'-Cyanine-d[CCAGAGCCACCTCCGCCTGAACC]-3'
```

The nucleotide and amino acid sequences of the ScFv 17 (IFN) are shown in FIG. 6 (SEQ ID NO: 1) and FIG. 7 (SEQ ID NO: 2). The main building blocks of the ScFv 17(IFN) are shown in FIG. 8.

Sequence Alignment VL and VH Domains of ScFv17 (IFN)

For the identification of potential cloning artifacts and sequencing errors we have compared a VH and VL sequence ScFv17 (INF) to the Kabat sequence database (Martin, 1996; http://www.bioinf.org.uk/abs/segtest.html). FIG. 9 shows VH and VL amino acid sequences. Residue labels and CDRs were defined according to Kabat. CDRs (complementary determining regions) are underlined.

Different BLAST-searches were performed for both VL and VH by using the 'BLASTP' search program (http://www.ncbi.nlm.nih.gov/BLAST). In FIG. 10 and FIG. 11, sequences are shown which align significantly with VH and VL ScFv17 (IFN). See Table 5 for correlation of the accession numbers with the SEQ ID NOS. The sequences of FIGS. 10 and 11 correspond to the indicated accession number or a subfragment thereof. The SEQ ID NOS correspond to the sequences shown in the Figures as indicated.

The data are summarized in Table 1. The scores for the VH varied from 83% to 90% for identical residues, and from 90% to 93% for chemically similar residues. For VL, analogous results were obtained. The scores for VL varied from 89% to 93% for identical residues and from 96% to 98% for similar residues. If CDR-loops were not taken into account, significantly higher scores were obtained (results not shown). It suggests that the greatest sequence diversity occurs in the CDR-loops for ScFv17 (IFN), while the FW region sequences for VL and VH are more conserved. Thus the single chain antibody to human interferon a2b (ScFv17 (IFN)) obtained from combinatorial antibody library has a unique primary structure (nucleotide and amino acid sequences) of the VH and VL domains.

TABLE 1

Summary of BLAST-search results

| SEQ ID NOS | Rank | Accessing Number | Ident./ Sim. | Gaps | Source |
|---|---|---|---|---|---|
| A. BLAST-search using ScFV 17 (IFN) $V_H$ sequence | | | | | |
| 13 | 1. | AAA16583 | 90%/93% | — | Immunoglobulin heavy chain |
| 14 | 2. | CAA10318 | 87%/91% | 1% | Single chain antibody scFv [*Mus musculus*] |
| 15 | 3. | AAA38145 | 86%/90% | 2% | Immunoglobulin mu-chain precursor |
| 16 | 4. | CAA62388 | 88%/91% | — | Antibody heavy chain variable region [*Mus musculus*] |
| 17 | 5. | AAA38411 | 84%/90% | 2% | Ig H-chain (VDJ-region) precursor |
| 18 | 6. | DZBA | 89%/92% | — | Chain A, crystal structure of phage library-derived single-chain Fv fragment 1 f9 in complex with turkey egg-white lysozyme |
| 19 | 7. | AAC53566 | 84%/90% | 1% | Ig heavy chain variable region [*Mus musculus*] |
| 20 | 8. | AAA16585 | 89%/92% | 1% | Immunoglobulin heavy chain |
| 21 | 9. | AAD47023 | 87%/92% | 1% | Immunoglobulin heavy chain variable region [*Mus musculus*] |
| 22 | 10. | S29594 | 83%/90% | 0% | Ig gamma chain (WM65) - mouse (fragment) |
| B. BLAST-search using ScFV 17 (IFN) $V_L$ sequence | | | | | |
| 23 | 1. | CAB60132 | 93%/97% | — | Anti-guinea pig C5 ScFv [synthetic construct] |
| 24 | 2. | CAA94520 | 91%/96% | — | scFv [*Mus musculus*] |
| 25 | 3. | CAD91925 | 93%/97% | — | Anti-human CD28 anti-human EpCAM ScFv antibody fragment [synthetic construct] |
| 26 | 4. | CAD30991 | 93%/97% | — | Anti-human EpCAM monoclonal antibody C215 [*Mus musculus*] |
| 27 | 5. | AAA38730 | 93%/98% | — | Ig kappa-chain VJ-region |
| 28 | 6. | BAC56972 | 93%/98% | — | Anti-glycyrrhetic acid antibody GA007 light chain [*Mus musculus*] |
| 29 | 7. | AAA38734 | 93%/98% | — | Ig kappa-chain VJ region |

TABLE 1-continued

Summary of BLAST-search results

| SEQ ID NOS | Rank | Accessing Number | Ident./Sim. | Gaps | Source |
|---|---|---|---|---|---|
| 30 | 8. | IMCPL | 90%/96% | — | Chain L, immunoglobulin Fab fragment |
| 31 | 9. | AAA72671 | 89%/96% | — | Ig light chain V region (V—C) |
| 32 | 10. | AAA38731 | 92%/97% | — | Ig kappa-chain VJ region |

Analysis of the Secondary mRNA Structure

For secretion we used a derivative from the natural secretory leader peptide from gene III structural protein of coliphage M13 (GenBank Accession NC_003287). Previously we have calculated the secondary structures of ScFv 17 (IFN) mRNA and showed that any stable secondary structures able to reduce the efficiency of initiation of translation did not come to light in the region of initiation of translation.

The programs used for mRNA secondary structure analysis was: RNAstructure and STAR.

Stable secondary structures in the region of translation initiation were compared and analyzed by programs efn and mfold.

Finally we showed that the 5'-terminus of the mRNA for ScFv17 (INF) cannot interfere with the AUG translation initiation codon and/or ribosome-binding site and it should not hamper effective translation initiation.

Theoretical Calculation of Some Characteristics of the ScFv 17(IFN)

Theoretical calculations from the ScFv17 (IFN) amino acid sequence for determining some protein characteristics were performed by Computer Program Vector NTA. The results are summarized in Tables 2 and 3.

TABLE 2

Physical properties of ScFv17 generated by Computer program NTA.

| Analysis | Entire Protein |
|---|---|
| Length | 279 aa |
| Molecular Weight | 29970.69 m.w. |
| 1 microgram = | 33.366 Moles |
| Molar Extinction coefficient | 49410 |
| 1 A[280] corr. to | 0.61 mg/ml |
| A[280] of 1 mg/ml | 1.65 AU |
| Isoelectric Point | 7.81 |
| Charge at pH 7 | 1.43 |

TABLE 3

Amino acid composition of ScFv17 generated by Computer program NTA.

| Amino Acid(s) | No. count | % by weight | % by frequency |
|---|---|---|---|
| Charged (RKHYCDE) | 71 | 31.28 | 25.45 |
| Acidic (DE) | 21 | 8.39 | 7.53 |
| Basic (KR) | 22 | 9.67 | 7.89 |
| Polar (NCOSTY) | 96 | 35.96 | 34.41 |
| Hydrophobic (AILFWV) | 83 | 29.46 | 29.75 |
| A Ala | 24 | 6.11 | 8.60 |
| C Cys | 4 | 1.39 | 1.43 |

TABLE 3-continued

Amino acid composition of ScFv17 generated by Computer program NTA.

| Amino Acid(s) | No. count | % by weight | % by frequency |
|---|---|---|---|
| D Asp | 11 | 4.19 | 3.94 |
| E Glu | 10 | 4.21 | 3.58 |
| F Phe | 8 | 3.78 | 2.87 |
| G Gly | 31 | 6.65 | 11.11 |
| H His | 8 | 3.55 | 2.87 |
| I Ile | 10 | 3.75 | -3.58 |
| K Lys | 16 | 6.69 | 5.73 |
| L Leu | 21 | 7.88 | 7.53 |
| M Met | 4 | 1.71 | 1.43 |
| N Asn | 8 | 3.02 | 2.87 |
| P Pro | 14 | 4.61 | 5.02 |
| O Gln | 16 | 6.68 | 5.73 |
| R Arg | 6 | 2.99 | 2.15 |
| S Ser | 28 | 8.41 | 10.04 |
| T Thr | 24 | 8.17 | 8.60 |
| V Val | 15 | 5.02 | 5.38 |
| W Trp | 5 | 2.92 | 1.79 |
| Y Tyr | 16 | 8.28 | 5.73 |
| B Asx | 19 | 7.21 | 6.81 |
| Z Glx | 26 | 10.89 | 9.32 |
| X Xxx | 0 | 0.00 | 0.00 |

Example 4

Purification and Refolding of the scFv17 (IFN) In Vitro

This example demonstrates successful refolding and some biochemical characteristics of the refolded ScFv to interferon a2b. The purification of inclusion bodies and oxidation of SH groups were performed as described by Kurucz et al., (Kurucz, et al. (1995) Mol. Immunol. 32, 1443-1452) with some modifications. Briefly, protein expression was induced as described above. Bacteria were lysed on ice with PBS (10 ml per 1 g w/w cells) containing 1 mg/ml hen's egg lysozyme for 20 min. and cell lysates were sonicated in the presence of 0.3% sodium deoxycholate (SDC) and precipitated by centrifugation at 16000 g for 10 min. Insoluble material was washed once with TE buffer (100 mM Tris-HCl, 2 mM EDTA, pH 8.0) containing 0.3% SDC, followed by two washes with TE buffer without SDC. At each washing step the pellet was completely resuspended by sonication. Partially purified inclusion bodies were pelleted by centrifugation and stored at −20° C. For in vitro oxidation of SH groups, inclusion bodies were solubilized in 50 mM Tris, pH 9.8 containing 2% sodium N-lauroylsarcosine (SLS, Sigma) at pellet:solvent (mg:ml) rations of 1:1 in open polypropylene flasks with rapid stirring for 15-24 hours at room temperature. Detergent was separated from protein by rapid extraction with an equal volume of n-butanol. A pellet of the oxidized ScFv was obtained by centrifugation of the suspension at 10000 g for 1 min. After centrifugation, the protein pellet was removed from the interface and washed once with 96% ethanol followed by three washes with PBS. These conditions provide the complete removal of detergent and butanol. For refolding, the protein pellet was dissolved in PBS containing 8 M urea (pH 8.0) and adjusted to a protein concentration of 0.5 mg/ml with the same buffer.

The refolding of oxidized scFv was performed by immobilizing metal ion affinity chromatography as follows. 2 ml of 50% Ni-NTA slurry (Ni-NTA Agarose, Qiagen) was added to 5 ml re-dissolved ScFv (0.5 mg/ml) and mixed gently by shaking for 30-40 min at room temperature. The protein-resin mixture was loaded onto an empty column and the flow-through was collected. The column was washed with 15 ml (approx. 20 column volumes) of wash buffer (100 mM NaH$_2$PO$_4$, 10 mM Tris-HCl, 8 M urea, pH 6.3). The flow rate was 0.4 ml/min. A linear gradient program utilizing PBS containing 8 M urea (pH 8.0) as buffer A and PBS (pH 8.0) as buffer B was run by an FPLC system (Pharmacia) as shown in Table 4

TABLE 4

| Time (min) | Flow Rate (ml/min) | Percent B |
|---|---|---|
| 0 | 0.4 | 0 |
| 15 | 0.4 | 0 |
| 135 | 0.4 | 100 |
| 150 | 0.4 | 100 |
| 151 | 0.0 | 0 |

Elution of the refolded ScFv was performed with elution buffer (50 mM NaH$_2$PO$_4$, 300 mM NaCl, 0.25 M imidazole, pH 8.5) in 5 column volumes at a flow rate of 0.4 ml/min. The elution profile is shown in FIG. 12. The different pools were analyzed by SDS-PAGE under reducing and non-reducing conditions (FIG. 13 and FIG. 14). The protein recovery from inclusion bodies was more than 50% and SDS-PAGE analysis (FIG. 13) showed that the recovered ScFv was more than 95% pure in a single step. After refolding in vitro, most of the recombinant protein migrated on SDS-PAGE more rapidly than the reduced protein and protein from inclusion bodies (FIG. 13). The shift in relative migration under reducing conditions showed that the ScFv refolded in an oxidized form. However, the refolded ScFv showed a high tendency for nonspecific aggregation in protein concentrations higher than 0.2 mg/ml (see gel filtration results).

Analytical Gel Filtration Chromatography

Analytical gel filtration chromatography was performed using a Sephacryl S-100 (Pharmacia) 10/30-gel filtration column. PBS buffer (pH 8.0) was used as the mobile phase, at a flow rate of 0.2 ml/min. Eluted fractions from the Ni-NTA column were applied to the Sephacryl column. The resulting chromatogram is shown in FIG. 15. The gel filtration profile gave four pools of single chain species, indicating the formation of ScFv dimeric and multimeric forms, where n>2. But the greater part (approx. 70%) of the ScFvs were present in elution fractions as a monomer form (30 kDa). All four fractions were analyzed by ELISA but only the peak emerging at 75 and 90 minutes was active in the immunoassay.

Binding Analysis

A. Estimation of Interferon-binding Activity for Matrix-immobilized ScFv17 (IFN)

ScFv renaturation was performed as described above by immobilizing metal ion affinity chromatography. Then 5 ml of crude interferon a2b (approx. 0.6 mg/ml) from E. coli cell lysates was diluted in PBS (pH 8.0) four times and passed over the ScFv-coupled Ni-NTA resin at a flow rate of 0.2 ml/min. PBS containing 20 mM imidazole was used to wash the column of any non specifically bound material, and when the absorbance at 280 nm returned substantially to the baseline, the wash buffer was changed to elution one (50 mM NaH$_2$PO$_4$, 300 mM NaCl, 0.25 M imidazole, pH 8.5). Eluted fractions were analyzed by SDS-PAGE (FIG). As shown in FIG. 16, the refolded ScFv that immobilized by hexahistidine tag to the Ni-NTA resin retains full interferon binding activity. It suggests that the refolding was performed successfully (the eluted complexes on SDS-PAGE contained equimolar quantity ScFv and IFN, FIG. 16).

B. Estimation of Interferon-binding Activity by ELISA

Binding activities of the refolded ScFv were determined by ELISA (Enzyme linked Immunosorbent Assay) on 96 well Titertek plates coated overnight at 4° C. with several dilutions of the refolded ScFv17 (IFN) and the same ScFv obtained from periplasm by IMAC as positive control. Protein concentrations were measured by adsorbance at 280 nm and aligned by dilution in 0.1 M bicarbonate buffer (pH 9.6) to 0.05 mg/ml. The wells were blocked for 1 hour with 3% milk powder in PBS at 37° C. All washes were with PBS containing 0.05% Tween 20 (Sigma). Interferon at 10 μg/ml in PBS containing 3% milk powder was added to the wells for 1 hour incubation at 37° C. After washes the mouse polyclonal anti-interferon antibodies (5-10 μg/ml) were added and the plate was incubated for 1 hour at 37° C. The polyclonal antibodies bound to the interferon-ScFv complexes were detected with HRP-conjugated anti-mouse monoclonal antibodies diluted at 1:2500 (Pharmacia). The peroxidase substrate TMB (Sigma) was used for development and the color was recorded at 450 nm. As shown in FIG. 17, ScFv refolded from inclusion bodies has the same immunological characteristics as the ScFv obtained from periplasm.

TABLE 5

Table of Sequences

| SEQ ID NO | Clone Name | Length | Type |
|---|---|---|---|
| 1 | ScFv 17 (IFN) | 843 | DNA |
| 2 | ScFv 17 (IFN) | 279 | Protein |
| 3 | VH | 117 | Protein |
| 4 | VL | 115 | Protein |
| 5 | PL1(+) | 62 | DNA |
| 6 | PL2(−) | 64 | DNA |
| 7 | R1 +) | 26 | DNA |
| 8 | R2(−) | 25 | DNA |
| 9 | seq primer | 23 | DNA |
| 10 | seq primer | 23 | DNA |
| 11 | 1_17662 | 117 | Protein |
| 12 | 1_24712 | 115 | Protein |
| 13 | 347913 | 114 | Protein |
| 14 | 4138227 | 115 | Protein |
| 15 | 195064 | 119 | Protein |
| 16 | 1518301 | 114 | Protein |
| 17 | 195748 | 119 | Protein |
| 18 | 11514087 | 113 | Protein |
| 19 | 2209229 | 118 | Protein |
| 20 | 347917 | 112 | Protein |
| 21 | 5690295 | 116 | Protein |
| 22 | 346840 | 117 | Protein |
| 23 | 6272271 | 114 | Protein |
| 24 | 1360012 | 115 | Protein |
| 25 | 31088009 | 114 | Protein |
| 26 | 20797200 | 114 | Protein |
| 27 | 196563 | 114 | Protein |
| 28 | 28316378 | 115 | Protein |
| 29 | 196571 | 114 | Protein |
| 30 | 230159 | 115 | Protein |
| 31 | 208622 | 115 | Protein |
| 32 | 196565 | 114 | Protein |
| 33 | M13 secretory | 14 | Protein |

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for recovery of a ScFv antibody having the sequence shown in SEQ ID NO:2 or having the sequences shown in SEQ ID NOS: 3 and 4 from *E. coli* inclusion bodies in biologically active form which comprises:

providing a transformed *E. coli* cell expressing a nucleic acid sequence encoding the ScFv antibody of SEQ ID NO:2 or SEQ ID NOS: 3 and 4 in the inclusion bodies;

solubilizing the inclusion bodies in a detergent to release the ScFv antibody;

oxidizing the released ScFv antibody to form disulfide bonds;

removing the detergent;

precipitating the oxidized ScFv antibodies;

dissolving the precipitated ScFv antibodies in a denaturing solution;

immobilizing the ScFv antibodies on a solid support;

renaturing ScFv antibodies on the solid support; and eluting the ScFv antibodies in biologically active form, wherein the ScFv antibody binds interferon α-2b.

2. The method of claim 1, wherein the detergent is N-lauroylsarcosine solution.

3. The method of claim 1, wherein the oxidation takes place in the presence of a $Cu^{2+}$ catalyst.

4. The method of claim 1, wherein the detergent is removed by butanol extraction.

5. The method of claim 1, wherein the precipitation is by centrifugation.

6. The method of claim 1, wherein the denaturing solution is a buffered urea solution.

7. The method of claim 1, wherein the renaturation is performed with a linear phosphate gradient.

8. The method of claim 1, wherein the solid support is Ni-NTA agarose.

9. An isolated ScFv 17 protein having the sequence shown in SEQ ID NO: 2.

10. An isolated ScFv17 protein having the amino acid sequence shown in SEQ ID NO:3 and the amino acid sequence shown in SEQ ID NO:4.

* * * * *